(12) United States Patent
Goldstein et al.

(10) Patent No.: US 10,441,568 B2
(45) Date of Patent: Oct. 15, 2019

(54) NITROXIDE RADICALS FOR THE TREATMENT OF DISEASES OF THE RESPIRATORY TRACT

(71) Applicants: Yissum Research Development Company of the Hebrew University of Jerusalem Ltd., Jerusalem (IL); Hadasit Medical Research Services and Development Ltd., Jerusalem (IL)

(72) Inventors: Sara Goldstein, Motza Elite (IL); Amram Samuni, Jerusalem (IL); Neville Berkman, Jerusalem (IL)

(73) Assignees: Yissum Research Development Company of the Hebrew University of Jerusalem Ltd., Jerusalem (IL); Hadasit Medical Research Services and Development Ltd., Jerusalem (IL)

( * ) Notice: Subject to any disclaimer, the term of this patent is extended or adjusted under 35 U.S.C. 154(b) by 196 days.

(21) Appl. No.: 15/560,170

(22) PCT Filed: Mar. 24, 2016

(86) PCT No.: PCT/IL2016/050320
§ 371 (c)(1),
(2) Date: Sep. 21, 2017

(87) PCT Pub. No.: WO2016/151591
PCT Pub. Date: Sep. 29, 2016

(65) Prior Publication Data
US 2018/0085347 A1    Mar. 29, 2018

Related U.S. Application Data

(60) Provisional application No. 62/138,550, filed on Mar. 26, 2015.

(51) Int. Cl.
*A61K 31/40* (2006.01)
*A61K 31/445* (2006.01)
*A61K 31/4015* (2006.01)
*A61K 31/45* (2006.01)

(52) U.S. Cl.
CPC .......... *A61K 31/40* (2013.01); *A61K 31/4015* (2013.01); *A61K 31/445* (2013.01); *A61K 31/45* (2013.01)

(58) Field of Classification Search
CPC .. A61K 31/40; A61K 31/4015; A61K 31/445; A61K 31/45
USPC ........................................................ 514/423
See application file for complete search history.

(56) References Cited

PUBLICATIONS

Communication Pursuant to Article 94(3) EPC dated Feb. 21, 2019 From the European Patent Office Re. Application No. 16718480.3. (4 Pages).

*Primary Examiner* — Yevgeny Valenrod

(57) ABSTRACT

Cyclic nitroxide compounds including, but not limited to, compounds having the general formula I:

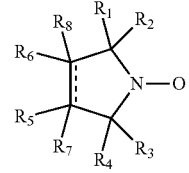

Formula I wherein the dashed line and $R_1$-$R_8$ are as defined herein, are disclosed herein for use in treating diseases and disorders of the respiratory tract and/or respiratory tract remodeling.

28 Claims, 15 Drawing Sheets
(7 of 15 Drawing Sheet(s) Filed in Color)

NITROXIDE RADICALS FOR THE TREATMENT OF DISEASES OF THE RESPIRATORY TRACT

RELATED APPLICATIONS

This application is a National Phase of PCT Patent Application No. PCT/IL2016/050320 having International filing date of Mar. 24, 2016, which claims the benefit of priority under 35 USC § 119(e) of U.S. Provisional Patent Application No. 62/138,550 filed on Mar. 26, 2015. The contents of the above applications are all incorporated by reference as if fully set forth herein in their entirety.

FIELD AND BACKGROUND OF THE INVENTION

The present invention, in some embodiments thereof, relates to therapy, and more particularly, but not exclusively, to treatment of diseases and disorders of the respiratory tract using nitroxide radicals.

Oxidative stress is one of the key components of inflammatory disorders. In particular, it has been widely reported to play a role in airway inflammation in various forms of asthma [Henricks & Nijkamp, *Pulm Pharmacol Ther* 2001, 14:409-420; Li et al., *Clin Immunol* 2003, 109 250-265; Riedl & Nel, *Curr Opin Allergy Clin Immunol* 2008, 8:49-56]. The reported association between oxidative stress and airway inflammation is reflected by production of reactive oxygen species (ROS) and reactive nitrogen species (RNS) [Andreadis et al., *Free Radic Biol Med* 2003, 35:213-225; Kharitonov & Barnes, *Curr Allergy Asthma Rep* 2003, 3:121-129; Maniscalco et al., *Inflamm Res* 2007, 56:58-69] and by an inverse correlation between endogenous levels of antioxidants and airway inflammatory processes [Mohan & Das, *Med Sci Res* 1997, 25:307-309; Dworski, *Thorax* 2000, 55:S51-S53; Rubin et al., *Am J Respir Crit Care Med* 2004, 169:393-398; Sackesen et al., *J Allergy Clin Immunol* 2008, 122:78-85; Kelly et al., *Lancet* 1999, 354:482-483; Picado et al., *Allergy* 2001, 56:43-49; Allan et al., *Clin Exp Allergy* 2010, 40:370-380].

Several decades of thorough research of biologically-relevant ROS have provided quite comprehensive knowledge and understanding of their chemical nature, the reactions of their formation and decay, the roles they play under physiological and pathophysiological conditions, and the mechanisms underlying their activities. So far, despite the available epidemiological, animal, molecular and immunological data indicating the association between antioxidants and asthma, the exact nature of the relationships and the potential for their therapeutic intervention remain unclear [Allan et al., *Clin Exp Allergy* 2010, 40:370-380].

The situation is even more complicated in the case of RNS, where nitric oxide (NO), an endogenous mediator having bronchodilating activity, may exhibit opposing effects. Nitric oxide is present in exhaled air and is increased in patients with asthma [Maniscalco et al., *Inflamm Res* 2007, 56:58-69; Massaro & Drazen, *Immunol Allerg Clin North Am* 1996, 16:735-751; Nevin & Broadley, *Pharmacol Ther* 2002, 95:259-293]. Persistently increased $O_2.^-$ (an ROS) and NO in asthma lead to the formation of peroxynitrite ($ONOO^-$), an RNS, and subsequent oxidation and nitration of essential cellular components, thus altering their function, and contributing to airway injury and inflammation [Andreadis et al., *Free Radic Biol Med* 2003, 35:213-225; Kharitonov & Barnes, *Curr Allergy Asthma Rep* 2003, 3:121-129]. On the other hand, inhalation of NO is used to treat newborns and critically ill asthmatic patients [Kinsella et al., *Lancet* 1992, 340:819-820; Kacmarek et al., *Am J Respir Crit Care Med* 1996, 153:128-135; Rishani et al., *Pediatr Pulmonol* 1999, 28:451-453; Gerlach et al., *Am J Respir Crit Care Med* 2003, 167:1008-1015]. The augmented availability of NO in the lungs may represent a plausible approach for the treatment of asthma; however, the mechanisms underlying the processes leading to the decreased expression of this molecule have not been fully elucidated [Nevin & Broadley, *Pharmacol Ther* 2002, 95:259-293; Lagente & Advenier, *Curr Opin Investig Drugs* 2004, 5:537-541; Antoniu, *Curr Opin Investig Drugs* 2010, 11:543-549].

Dietary supplementation of common antioxidants has been tested for several decades in an attempt to prevent or treat asthma and other airway inflammatory disorders [Locksley, *Cell* 2010, 140:777-783; Li et al., *Clin Immunol* 2003, 109 250-265; Andreadis et al., *Free Radic Biol Med* 2003, 35:213-225; Picado et al., *Allergy* 2001, 56:43-49; McNally, *J Ir Med Assoc* 1953, 33:175-178; Braskett & Riedl, *Curr Opin Allergy Clin Immunol* 2010, 10:34-41; Fogarty et al., *Clin Exp Allergy* 2003, 33:1355-1359; Greene, *Nutrition* 1999, 15:899-907; Kelly, *Proc Nutr Soc* 2005, 64:510-526]. However, the reported efficacy of antioxidant therapy is still equivocal [Misso & Thompson, *Redox Rep* 2005, 10:247-255; Murr et al., *Med Hypotheses* 2005, 64:973-977] and in many cases disappointing [Allan et al., *Clin Exp Allergy* 2010, 40:370-380; Dunstan et al., *Clin Exp Allergy* 2007, 37:180-187; Greene, *J Am Coll Nutr* 1995, 14:317-324; Hernandez et al., *Inhal Toxicol* 2009, 21:173-181].

Cyclic nitroxides are relatively stable free radicals which can undergo one-electron redox reactions to form the respective hydroxylamine and/or oxoammonium compounds, as depicted in Scheme 1 below for 2,2,6,6-tetramethyl-piperidine-N-oxyl (Tempo), a commonly used nitroxide:

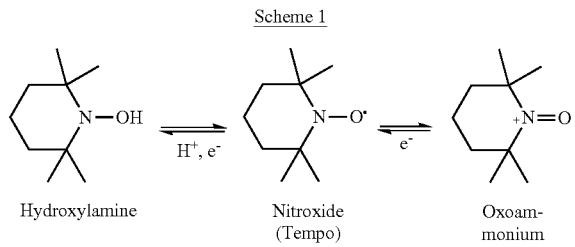

Scheme 1

Hydroxylamine     Nitroxide (Tempo)     Oxoammonium

Cyclic hydroxylamines have very weak O—H bonds, so cyclic nitroxides rarely participate in hydrogen abstraction reactions. However, being radicals, the nitroxides react rapidly with other radicals including $HO_2$. [Goldstein et al., *J Am Chem Soc* 2003, 125:789-795; Goldstein et al., *J Phys Chem A* 2006, 110:3679-3685], carbon-centered radicals [Asmus et al., *Int J Radiat Biol Relat Stud Phys Chem Med* 1976, 29:211-219; Beckwith et al., *J Am Chem Soc* 1992, 114:983-4992; Bowry & Ingold, *J Am Chem Soc* 1992, 114:4992-4996], peroxyl radicals [Goldstein & Samuni, *J Phys Chem A* 2007, 111:1066-1072], thiyl radicals [Goldstein et al., *J Phys Chem A* 2008, 112:8600-8605], .OH [Samuni et al., *J Am Chem Soc* 2002, 124:8719-8724], $.NO_2$ [Goldstein et al., *J Am Chem Soc* 2003, 125:8364-8370] and $CO_3.^-$ [Goldstein et al., *Chem Res Toxicol* 2004, 17:250-257] without giving rise to secondary radicals. In addition, nitroxide radicals inhibit free radical formation via the Fenton reaction by oxidizing reduced metal ions such as $Cu^I$ or Fe$^{II}$ [Samuni et al., *Biochemistry* 1991, 30:555-561; Bar-On et al., *J Am Chem Soc* 1999, 121:8070-8073].

Nitroxides have been reported to exhibit anti-inflammatory, radioprotective, anti-mutagenic, anti-hypertensive, and anticancer activities, with Tempol (4-hydroxy-2,2,6,6-tetramethylpiperidin-1-oxyl) being a particularly widely studied nitroxide [Soule et al., *Free Radic Biol Med* 2007, 42:1632-1650; Soule et al., *Antioxid Redox Signal* 2007, 9:1731-1743].

Nitroxides have been reported to protect experimental animals against hyperoxia-induced brain damage [Howard et al., *J Neurochem* 1996, 67:2045-2050], experimental pancreatitis [Sledzinski et al., *Int J Pancreatol* 1995, 18:153-160], closed head injury induced by mechanical trauma [Beit-Yannai et al., *Brain Res* 1996, 717:22-28], and injuries associated with excessive NO production such as those resulting from multiple organ failure, transient cerebral ischemia, carrageenan-induced pleurisy, and dinitrobenzenesulfonic acid-induced colitis [Wilcox & Pearlman, *Pharmacol Rev* 2008, 60:418-469; Wilcox, *Pharmacol Ther* 2010, 126:119-145].

Nitroxides have also been reported to attenuate oxidative damage in various models such as lipid peroxidation in liver microsomes [Miura et al., *Arch Biochem Biophys* 1993, 300:148-156; Antosiewicz et al., *Free Radic Biol Med* 1997, 22:249-255; Cighetti et al., *Chem Phys Lipids* 1997, 88:97-106], tumor necrosis factor cytotoxicity [Pogrebniak et al., *J Surg Res* 1991, 50:469-474], thymocyte apoptosis [Slater et al., *Biochem J* 1995, 306:771-778], and post-ischemic reperfusion injury [Beaulieu et al., *J Cereb Blood Flow Metab* 1998, 18:1022-1031; Zeltcer et al., *Free Radic Biol Med* 2002, 32:912-919; Zeltcer et al., *Free Radic Res* 1997, 27:627-635].

Krishna et al. [*J Med Chem* 1998, 41:3477-3492] reported that the protective effects of cyclic nitroxides against oxidative damage are not dependent on ring size, but are enhanced by basic side chains.

U.S. Pat. No. 6,605,619 describes oxazolidine-derived and piperidine-derived nitroxides and hydroxylamines, and uses thereof for treating or preventing conditions such as inflammation, cancer, diabetes, cardiovascular disorders, weight gain, polyps and/or chronic pain.

U.S. Patent Application Publication No. 2012/0263650 describes compounds comprising a non-steroidal anti-inflammatory drug moiety and a nitroxide-containing moiety such as a TEMPO moiety, as well as uses thereof in the treatment of conditions such as inflammation, cancer, diabetes, cardiovascular disorders, weight gain, asthma, polyps and/or chronic pain.

U.S. Patent Application Publication No. 2008/0139525 describes synergistic combinations of a superoxide dismutase mimetic such as manganese compound or nitroxides with a selenium compound, for treating inflammatory, autoimmune, vascular and cardiovascular conditions.

Additional background art includes Arieli et al. [*Free Radic Res* 2008, 42:114-123], Aronovitch et al. [*Free Radic Biol Med* 2007, 42:1317-1325], Barnes [*Proc Am Thorac Soc* 2004, 1:264-268], Beers & Morrisey [*J Clin Invest* 2011, 121:2065-2073], Bergeron et al. [*Can Respir J* 2010, 17:e85-e93], Cho et al. [*J Allergy Clin Immunol* 2004, 114:429-435], Exo et al. [*J Neurotrauma* 2009, 26:2403-2408], Jubeh et al. [*J Drug Target* 2006, 14:155-163], Kirkham & Rahman [*Pharmacol Therapeut* 2006, 111:476-494], Komarov et al. [*Biochem Biophys Res Commun* 1994, 201:1035-1042], Krishna et al. [*PNAS USA* 1992, 89:5537-5541], Krishna et al. [*J Biol Chem* 1996, 271:26018-26025], Iannonea et al. [*Biochem Biophys Acta* 1989, 991:90-96], Mabalirajan et al. [*J Appl Physiol* 2009, 107:1285-1292], Mitchell et al. [*Biochemistry* 1990 29:2802-2807], Offer & Samuni [*Free Radic Biol Med* 2002, 32:872-881], Postma & Timens [*Proc Am Thorac Soc* 2006, 3:434-439], Reddan et al. [*Exp. Eye Res* 1993, 56:543-554], Samuni & Barenholz [*Free Radic Biol Med* 1997, 22:1165-1174], Samuni & Barenholz [*Free Radic Biol Med* 2003, 34:177-185], Samuni et al. [*Biochemistry* 1991, 30:555-561], Samuni et al. [*J Biol Chem* 1998, 263:17921-17924], Swartz et al. [*Biochem Biophys Acta* 1986, 888:82-90], Takeshita et al. [*Biochem Biophys Res Commun* 1991, 177:874-880], Utsumi et al. [*Biochem Biophys Res Commun* 1990, 172:1342-1348], Wagner et al. [*Clin Exp Allergy* 2008, 38:501-511], Wasserman et al. [*Langmuir* 2007, 23:1937-1947] and Zuoa et al. [*Mol Immunol* 2013, 56:57-63].

SUMMARY OF THE INVENTION

According to an aspect of some embodiments of the invention, there is provided a compound having the general formula I:

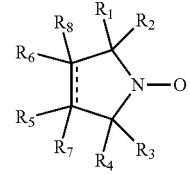

Formula I wherein:

the dashed line denotes a saturated bond or an unsaturated bond, wherein when the dashed line denotes an unsaturated bond, $R_7$ and $R_8$ are absent;

$R_1$-$R_4$ are each independently a $C_{1-4}$-alkyl, or alternatively, $R_1$ and $R_2$, and/or $R_3$ and $R_4$, together form a 3-7-membered alicyclic ring; and $R_5$-$R_8$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, for use in treating a disease or disorder of the respiratory tract.

According to an aspect of some embodiments of the invention, there is provided a cyclic nitroxide compound for use in treating a disease or disorder associated with respiratory tract remodeling.

According to an aspect of some embodiments of the invention, there is provided a cyclic nitroxide compound for use in treating asthma, chronic obstructive pulmonary disease (COPD), pulmonary fibrosis and/or lung cancer.

According to some embodiments of the invention, the abovementioned cyclic nitroxide compound has general formula II:

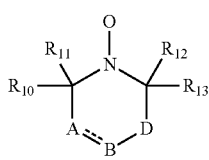

Formula II wherein:
the dashed line denotes a saturated bond or unsaturated bond;

$R_{10}$-$R_{13}$ are each independently a $C_{1-4}$-alkyl, or alternatively, $R_{10}$ and $R_{11}$, and/or $R_{12}$ and $R_{13}$, together form a 3-7-membered alicyclic ring;

A is selected from the group consisting of $CR_{14}R_{15}$, C=O, O, S and $NR_{16}$ when the dashed line denotes a saturated bond, and from the group consisting of $CR_{17}$ and N when the dashed line denotes an unsaturated bond;

B is selected from the group consisting of $CR_{18}R_{19}$, C=O, O, S and $NR_{20}$ when the dashed line denotes a saturated bond, and from the group consisting of $CR_{21}$ and N when the dashed line denotes an unsaturated bond;

D is selected from the group consisting of $CR_{21}R_{22}$, C=O, O, S and $NR_{23}$, or alternatively, D is absent; and $R_{14}$-$R_{23}$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine and amino, or alternatively, any one of $R_{18}$-$R_{20}$ and any one of $R_{14}$-$R_{16}$ and $R_{21}$-$R_{23}$ together form an aromatic, alicyclic or heteroalicyclic ring.

According to some embodiments of the invention, one or more of $R_{14}$, $R_{15}$, $R_{18}$, $R_{19}$, $R_{21}$ and $R_{22}$ is selected from the group consisting of C-amido and hydroxy.

According to some embodiments of the invention, $R_{18}$ is selected from the group consisting of C-amido and hydroxy.

According to some embodiments of the invention, one or more, or each, of $R_{10}$-$R_{13}$ is methyl.

According to some embodiments of the invention, $R_{14}$-$R_{17}$ and $R_{19}$-$R_{23}$ are each hydrogen.

According to some embodiments of the invention, the compound is selected from the group consisting of 3-carbamoyl-2,2,5,5-tetramethyl-pyrrolidin-1-oxyl, 3-carbamoyl-2,2,5,5-tetramethyl-3-pyrrolin-1-oxyl and 4-hydroxy-2,2,6,6-tetramethyl-piperidin-1-oxyl.

According to some embodiments of the invention, the abovementioned dashed line denotes a saturated bond.

According to some of any of the embodiments of the invention relating to general formula I, one or more of $R_5$-$R_8$ is C-amido.

According to some of any of the embodiments of the invention relating to general formula I, $R_5$ is C-amido.

According to some of any of the embodiments of the invention relating to general formula I, the C-amido is —C(=O)NH$_2$.

According to some of any of the embodiments of the invention relating to general formula I, at least one, or each, of $R_1$-$R_4$ is methyl.

According to some of any of the embodiments of the invention relating to general formula I, $R_6$ is hydrogen, and each of $R_7$ and $R_8$ is either hydrogen or absent.

According to some embodiments of the invention, the compound is 3-carbamoyl-2,2,5,5-tetramethyl-pyrrolidin-1-oxyl.

According to some embodiments of the invention, the disease or disorder of the respiratory tract is an inflammatory disease or disorder of the respiratory tract.

According to some embodiments of the invention, the disease or disorder of the respiratory tract is associated with respiratory tract remodeling.

According to some embodiments of the invention, the disease or disorder of the respiratory tract is selected from the group consisting of idiopathic interstitial pneumonia, autoimmune-related pulmonary fibrosis, drug-induced interstitial lung disease, tuberculosis, chronic obstructive pulmonary disease (COPD), chronic asthma, emphysema, acute lung injury, acute respiratory distress syndrome, and Birt-Hogg-Dube syndrome.

According to some embodiments of the invention, the disease or disorder of the respiratory tract is a lung disease or disorder.

According to some embodiments of the invention, the lung disease or disorder is selected from the group consisting of an obstructive lung disease or disorder and an interstitial lung disease or disorder.

According to some embodiments of the invention, the obstructive lung disease or disorder is selected from the group consisting of asthma, bronchitis, bronchiectasis, and chronic obstructive pulmonary disease (COPD).

According to some embodiments of the invention, the interstitial lung disease is selected from the group consisting of pulmonary fibrosis, hypersensitivity pneumonitis, pneumoconiosis, infectious interstitial lung diseases, drug-induced interstitial lung diseases, interstitial lung diseases associated with a connective tissue disease, sarcoidosis, acute interstitial pneumonia, idiopathic interstitial pneumonia, anti-synthetase syndrome, and granulomatosis with polyangiitis.

According to some embodiments of the invention, the disease or disorder of the respiratory tract is associated with a hypersensitivity reaction.

According to some embodiments of the invention, the disease or disorder of the respiratory tract is a cancer.

According to some embodiments of the invention, the treating comprises oral and/or intranasal administration of the compound.

According to some embodiments of the invention, the treating does not comprise (e.g., is devoid of) administration of a selenium-containing compound.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a bar graph showing residual concentrations of the nitroxides 3-CP and TPL in whole blood of individual mice (6 or 7 mice per treatment group) fed chow with 1 weight percent nitroxide, the blood being taken during sensitization stage (S) or challenge stage (C) of induction of asthma with ovalbumin (OVA).

FIG. 2 is a graph showing residual concentration of 3-CP in mouse blood and lung tissue as function of time after nasal instillation of 3-CP.

Figure 3:
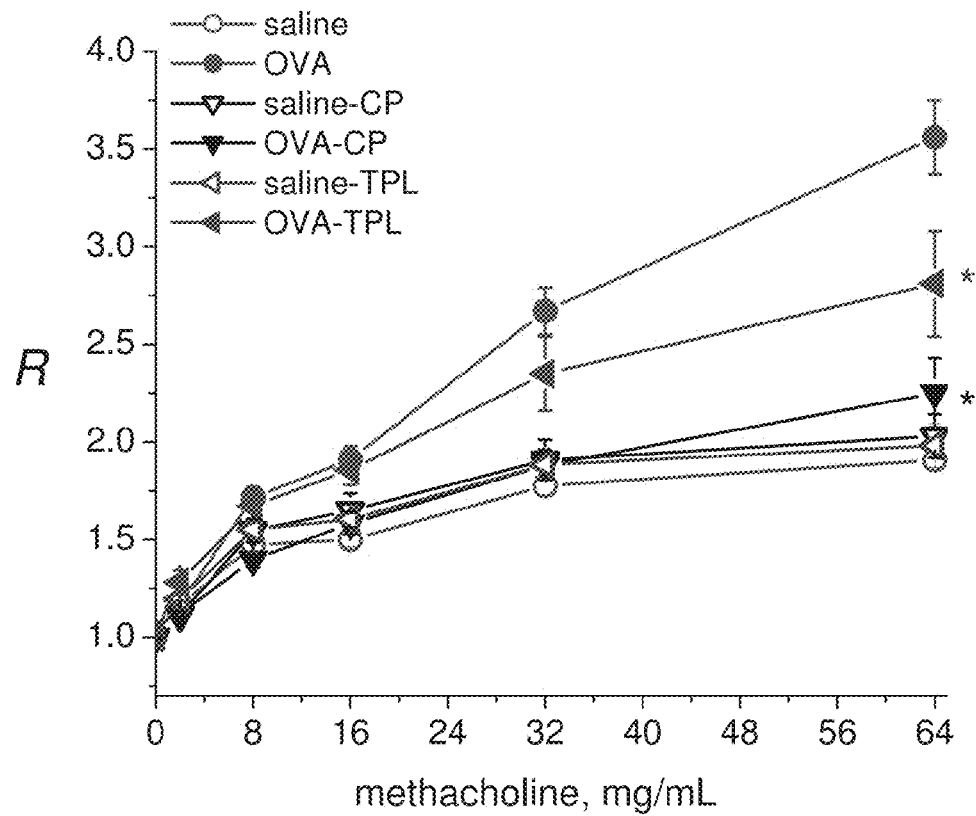

FIG. 3 is a graph showing lung resistance (R) of mice treated with ovalbumin (OVA) to induce asthma or with saline as a control, with and without oral administration (1 weight percent in chow) of the nitroxides 3-CP (CP) or TPL, as a function of concentration of administered methacholine (each value represents means±SEM for 8-10 mice; *$p<0.05$ vs. OVA without nitroxide; methacholine administered during lung resistance measurement).

Figure 4:
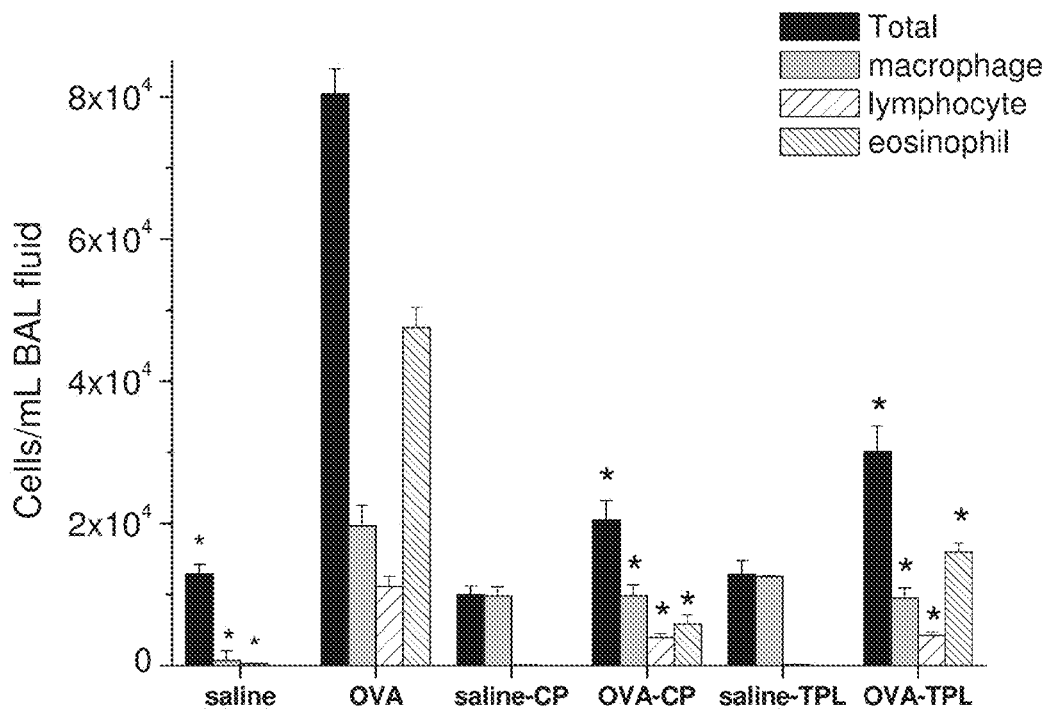

FIG. 4 is a bar graph showing levels of total inflammatory cells, macrophages, lymphocytes and eosinophils in bronchoalveolar lavage (BAL) fluid from mice treated for 4 weeks with ovalbumin (OVA) or saline alone, or with oral administration (1 weight percent in chow) of the nitroxides 3-CP (CP) or TPL (each value represents means±SEM for 8-10 mice; *$p<0.05$ vs. OVA without nitroxide).

Figure 5:
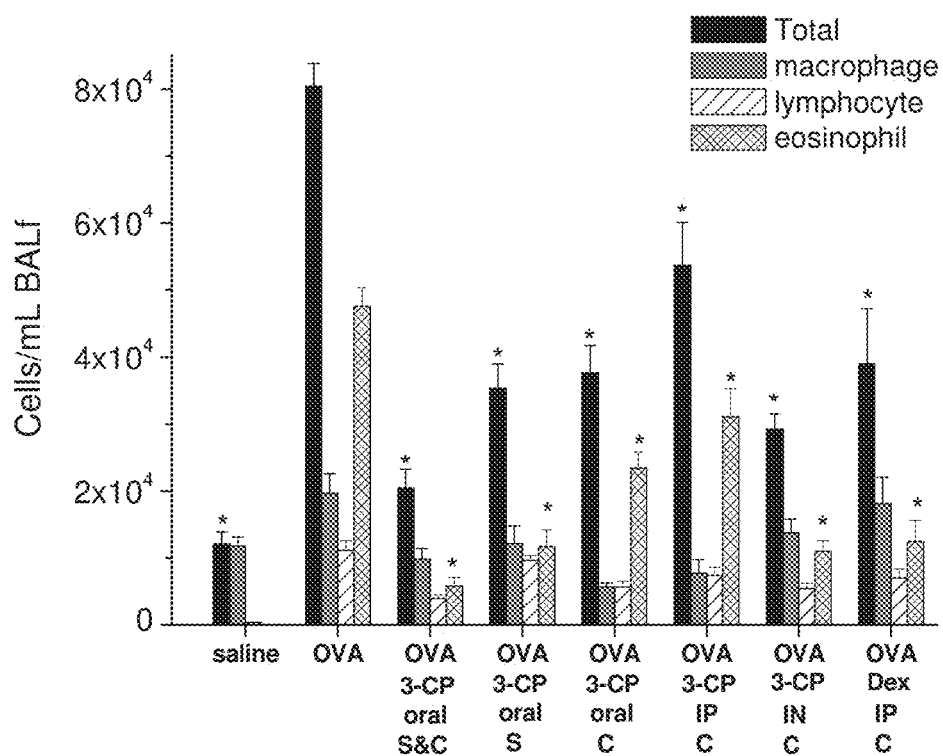

FIG. 5 is a bar graph showing levels of total inflammatory cells, macrophages, lymphocytes and eosinophils in bronchoalveolar lavage (BAL) fluid from mice treated with ovalbumin alone (OVA) or ovalbumin with dexamethasone (Dex) or 3-CP, or with saline; 3-CP or dexamethasone administered by oral, intraperitoneal (IP) or intranasal (IN) route, during sensitization stage (S) and/or challenge stage (C) of ovalbumin treatment (each value represents means±SEM for 8-10 mice; *$p<0.05$ vs. OVA without Dex or 3-CP).

Figure 6:
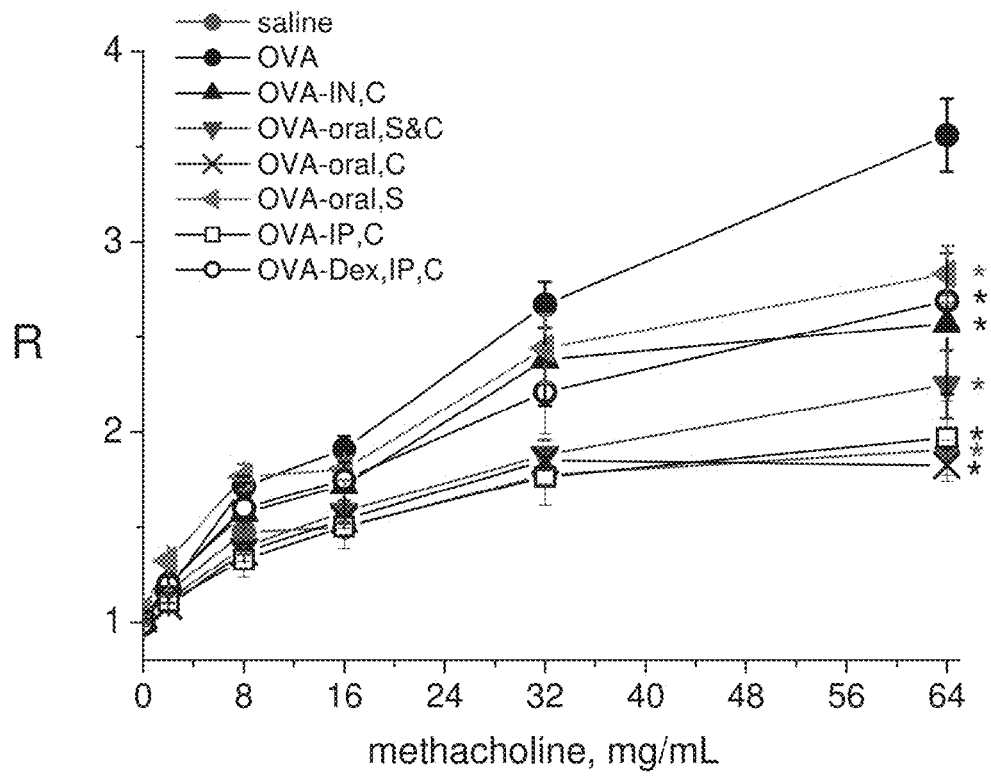

FIG. 6 is a graph showing lung resistance (R) as a function of concentration of administered methacholine, for mice treated with ovalbumin (OVA) to induce asthma or with saline as a control, with and without administration of 3-CP by oral administration (1 weight percent in chow), intraperitoneal (IP) injection (~300 mg/kg) or intranasal (IN) instillation (~300 mg/kg), or with intraperitoneal administration of 1 mg/kg dexamethasone, during sensitization stage (S) and/or challenge stage (C) of ovalbumin treatment (each value represents means±SEM for 8-10 mice; *$p<0.05$ vs. OVA without nitroxide; methacholine administered during lung resistance measurement).

FIGS. 7A-7E are each bar graphs showing concentration (in ng or pg per ml) of the cytokines IL-4 (FIG. 7A), IL-5 (FIG. 7B), INF-γ (FIG. 7C), IL-13 (FIG. 7D) and TGF-β1 (FIG. 7E) in bronchoalveolar lavage fluid (BALf) of treated mice with ovalbumin (OVA) to induce asthma or with saline as a control, with and without administration of 3-CP by oral administration (1 weight percent in chow), intraperitoneal (IP) injection (~300 mg/kg) or intranasal (IN) instillation (~300 mg/kg), or with intraperitoneal administration of 1 mg/kg dexamethasone, during sensitization stage (S) and/or challenge stage (C) of ovalbumin treatment (each value represents means±SEM for 8-10 mice; *$p<0.05$ vs. OVA without Dex or 3-CP).

Figure 8:
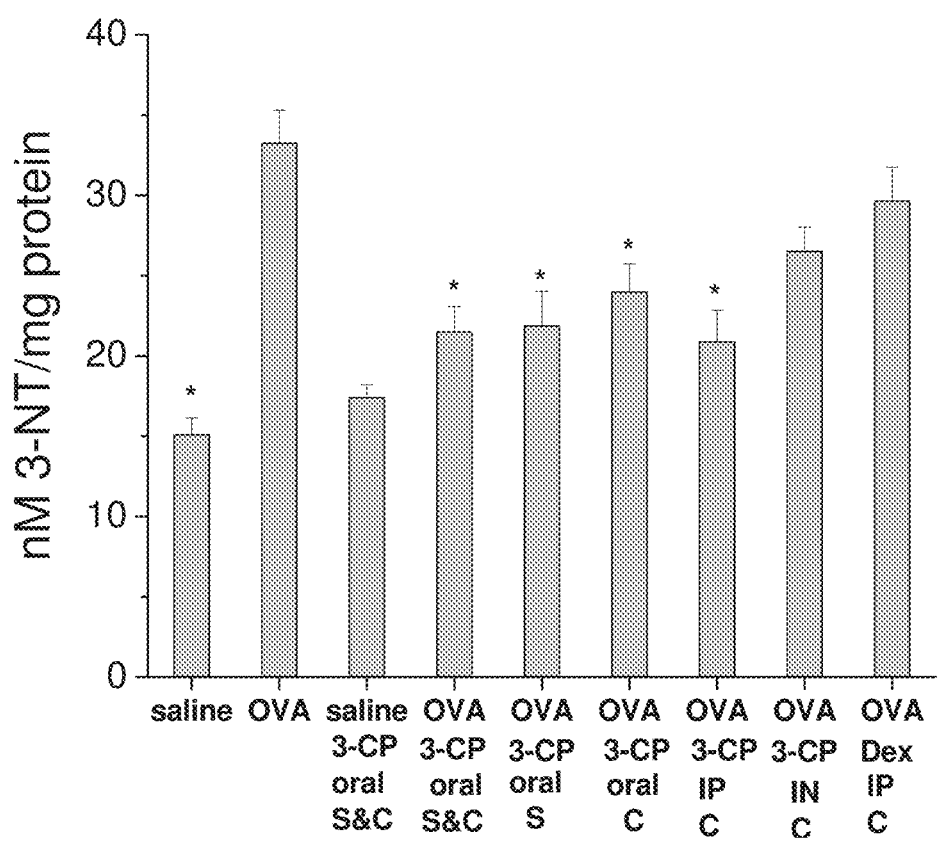

FIG. 8 is a bar graph showing concentration (in nM per mg protein) of 3-nitrotyrosine (3-NT) in lung tissue from mice treated with ovalbumin (OVA) to induce asthma or with saline as a control, with and without administration of 3-CP by oral administration (1 weight percent in chow), intraperitoneal (IP) injection (~300 mg/kg) or intranasal (IN) instillation (~300 mg/kg), or with intraperitoneal administration of 1 mg/kg dexamethasone, during sensitization stage (S) and/or challenge stage (C) of ovalbumin treatment (each value represents means±SEM for 8-10 mice; *$p<0.05$ vs. OVA without Dex or 3-CP).

Figure 9:
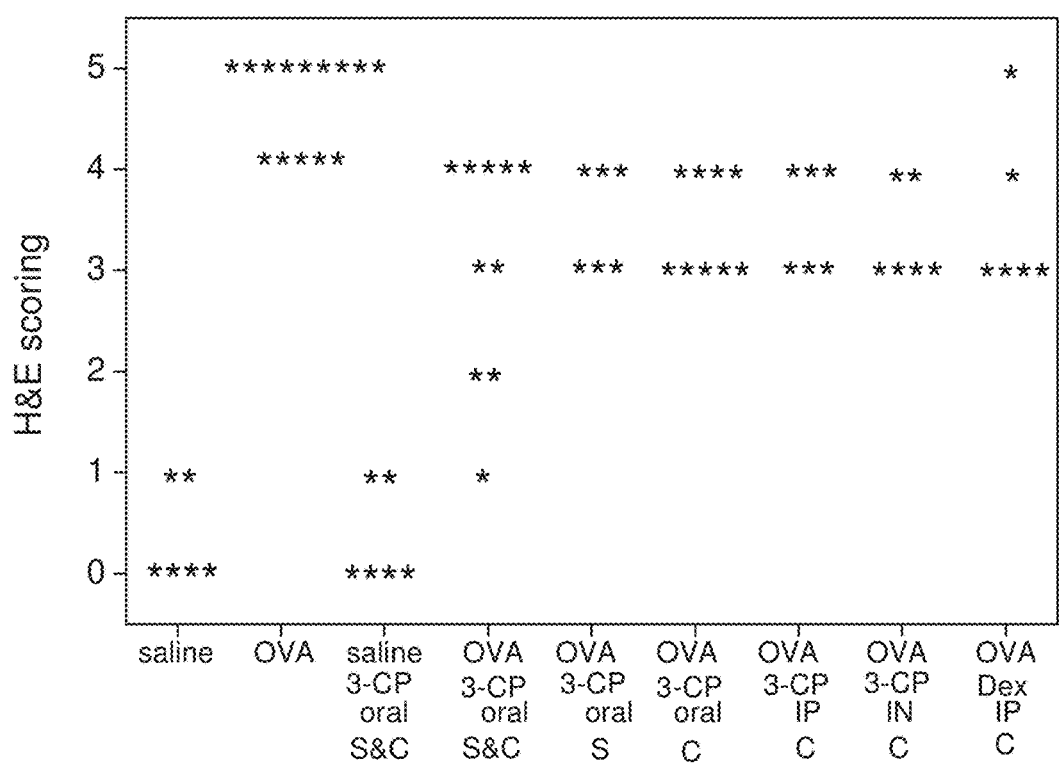

FIG. 9 is a graph showing the distribution of pathological scores of lung tissue stained with hematoxylin and eosin (H & E) from mice treated with ovalbumin (OVA) to induce asthma or with saline as a control, with and without administration of 3-CP by oral administration (1 weight percent in chow), intraperitoneal (IP) injection (~300 mg/kg) or intranasal (IN) instillation (~300 mg/kg), or with intraperitoneal administration of 1 mg/kg dexamethasone, during sensitization stage (S) and/or challenge stage (C) of ovalbumin treatment ($p<0.001$ for saline vs. OVA and OVA vs. OVA 3-CP oral (S&C); $p=0.007$ for OVA vs. OVA 3-CP oral (C); $p=0.046$ for OVA vs. OVA 3-CP oral (S); $p=0.046$ for OVA vs. OVA 3-CP IP (C); $p=0.011$ for OVA vs. OVA 3-CP IN (C); $p=0.046$ for OVA vs. OVA Dex IP (C)).

Figure 10:
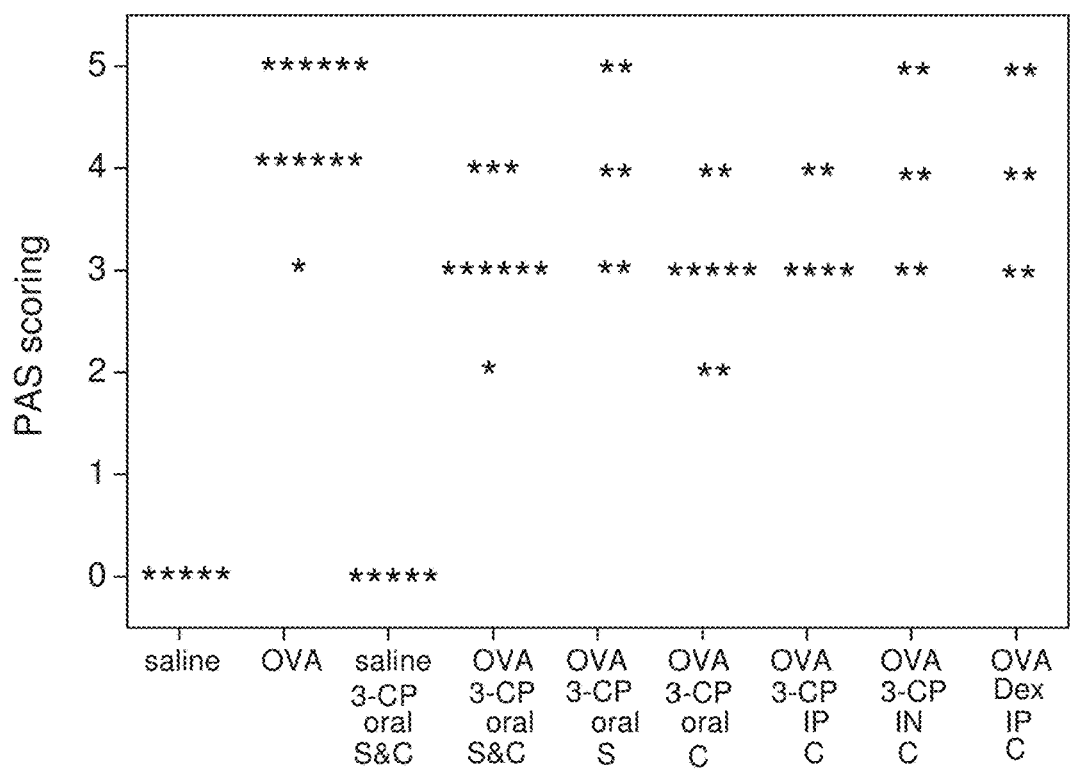

FIG. 10 is a graph showing the distribution of pathological scores of lung tissue stained with periodic acid-Schiff (PAS) stain, from mice treated with ovalbumin (OVA) to induce asthma or with saline as a control, with and without administration of 3-CP by oral administration (1 weight percent in chow), intraperitoneal (IP) injection (~300 mg/kg) or intranasal (IN) instillation (~300 mg/kg), or with intraperitoneal administration of 1 mg/kg dexamethasone, during sensitization stage (S) and/or challenge stage (C) of ovalbumin treatment ($p<0.001$ for saline vs. OVA; $p=0.003$ for OVA vs. OVA 3-CP oral (S&C); $p=0.002$ for OVA vs. OVA 3-CP oral (C); $p=0.046$ for OVA vs. OVA 3-CP IP (C)).

Figure 11:
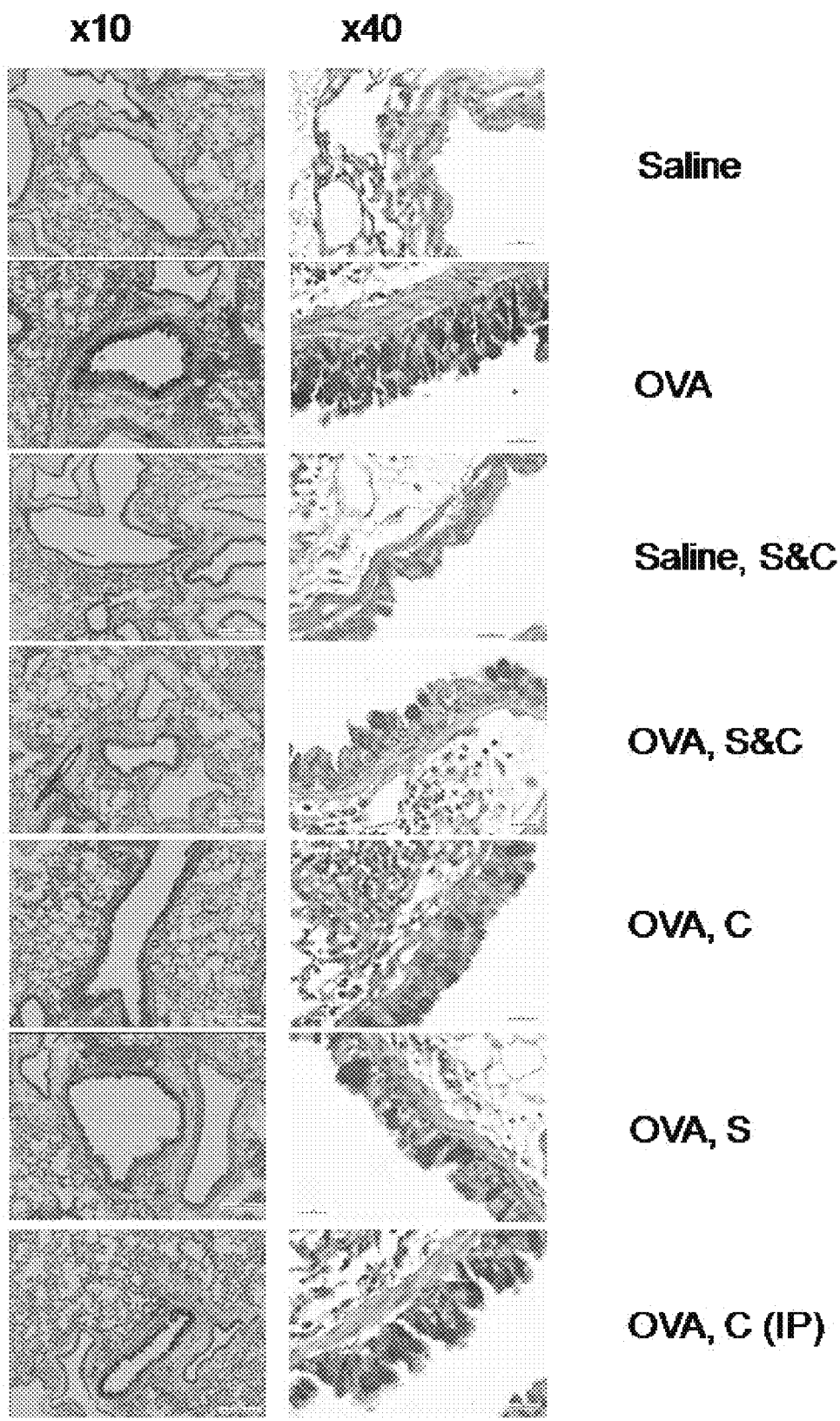

FIG. 11 presents images at ×10 and ×40 magnification of representative samples of PAS-stained lung tissue from mice treated with ovalbumin (OVA) to induce asthma or with saline as a control, with and without oral administration of 3-CP (1 weight percent in chow) during sensitization stage (S) and/or challenge stage (C) of ovalbumin treatment, or with intraperitoneal administration of 3-CP (~300 mg/kg) during the challenge stage (C (IP)).

Figure 12:
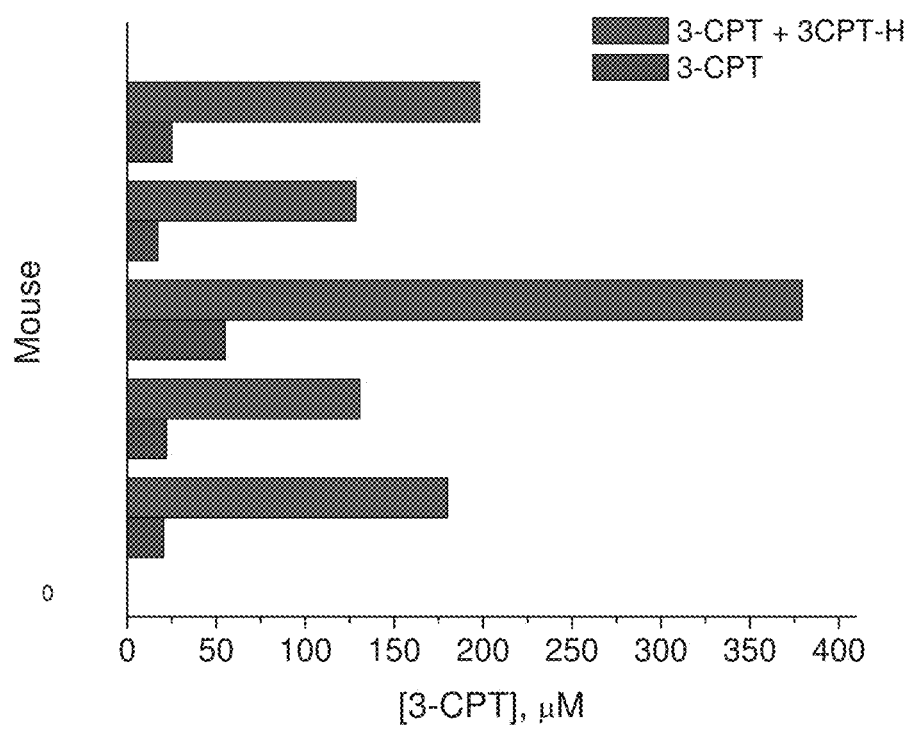

FIG. 12 is a bar graph showing steady state concentrations of the nitroxide 3-CPT and total concentration of 3-CPT and its corresponding hydroxylamine (3-CPT+3CPT-H) in blood of individual mice fed chow with 0.7 weight percent 3-CPT.

Figure 13:
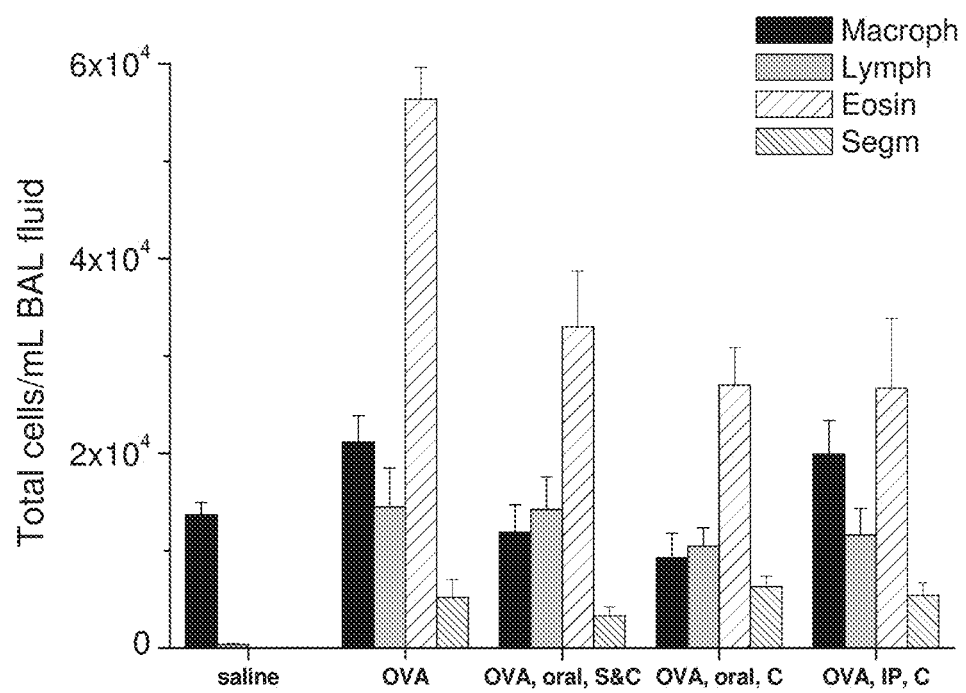

FIG. 13 is a bar graph showing levels of macrophages (Macroph), lymphocytes (Lymph), eosinophils (Eosin) and neutrophils (Segm) in bronchoalveolar lavage (BAL) fluid from mice treated with saline or ovalbumin alone (OVA) or ovalbumin with 3-CPT administered by oral (0.7 weight percent 3-CPT in chow) or intraperitoneal (IP; 300 mg/kg) administration during sensitization stage (S) and/or challenge stage (C) of ovalbumin treatment.

Figure 14:
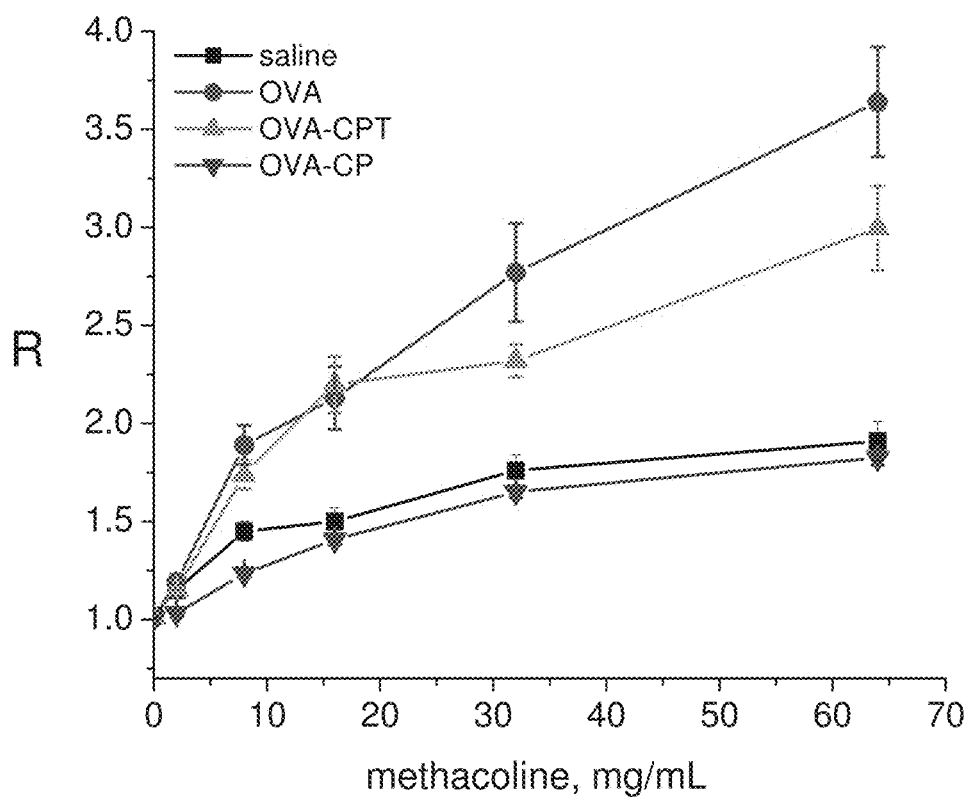

FIG. 14 is a graph showing lung resistance (R) as a function of concentration of administered methacholine, for mice treated with ovalbumin alone (OVA) or with oral administration of 3-CP (1 weight percent in chow; OVA-CP) or 3-CPT (0.7 weight percent in chow; OVA-CPT), or with saline as a control (each value represents means±SEM for 10 mice; *p<0.05 vs. OVA alone according to ANOVA; methacholine administered during lung resistance measurement).

Figure 15A:
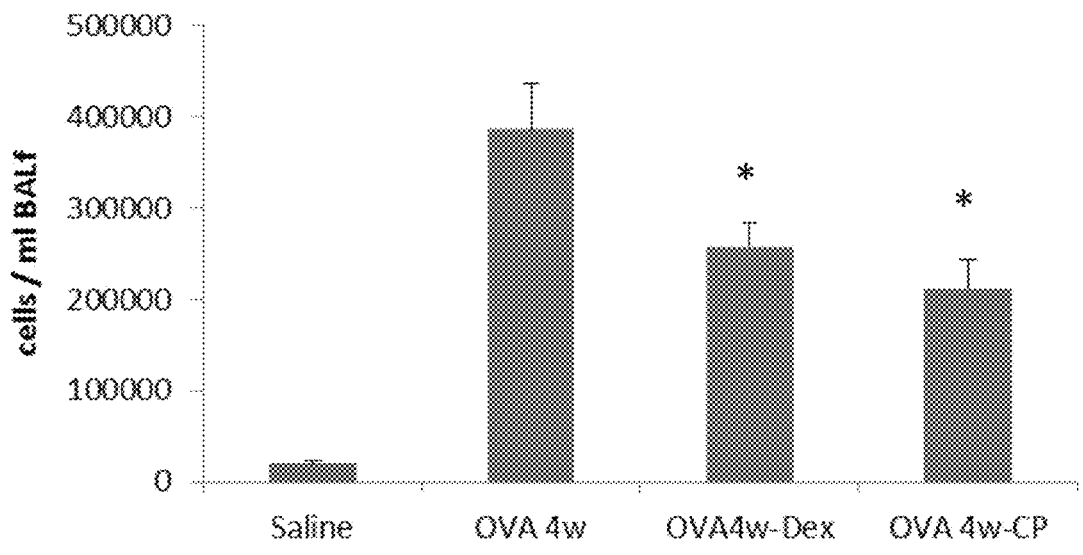
Figure 15B:
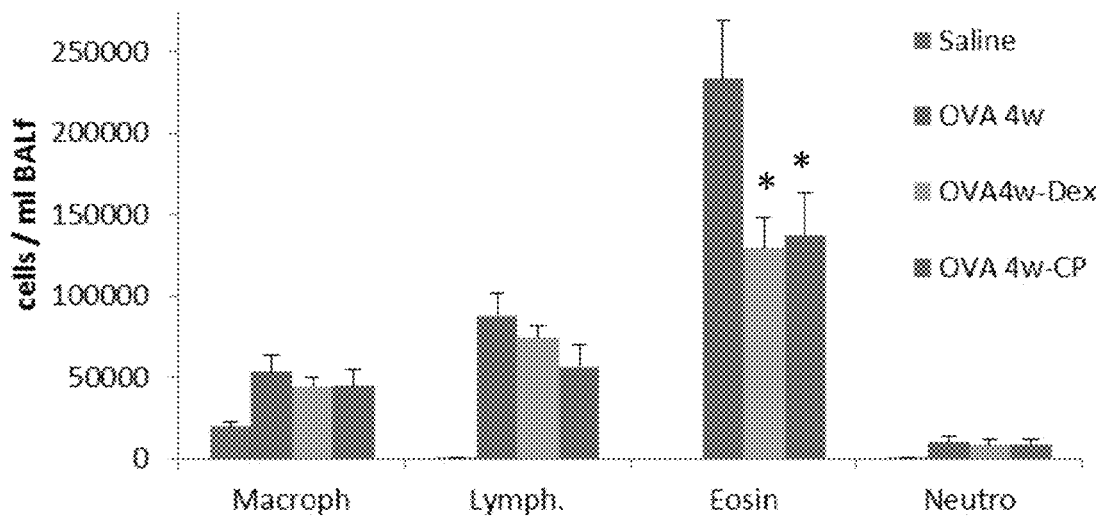

FIGS. 15A and 15B are each bar graphs showing levels of total inflammatory cells (FIG. 15A) and macrophages (Macroph), lymphocytes (Lymph.), eosinophils (Eosin) and neutrophils (Neutro) (FIG. 15B) in bronchoalveolar lavage (BAL) fluid from mice treated for 4 weeks with ovalbumin alone (OVA 4w) or ovalbumin with dexamethasone (OVA4w-Dex) or 3-CP (OVA 4w-CP), or with saline (*p<0.05 vs. OVA 4w).

Figure 16:
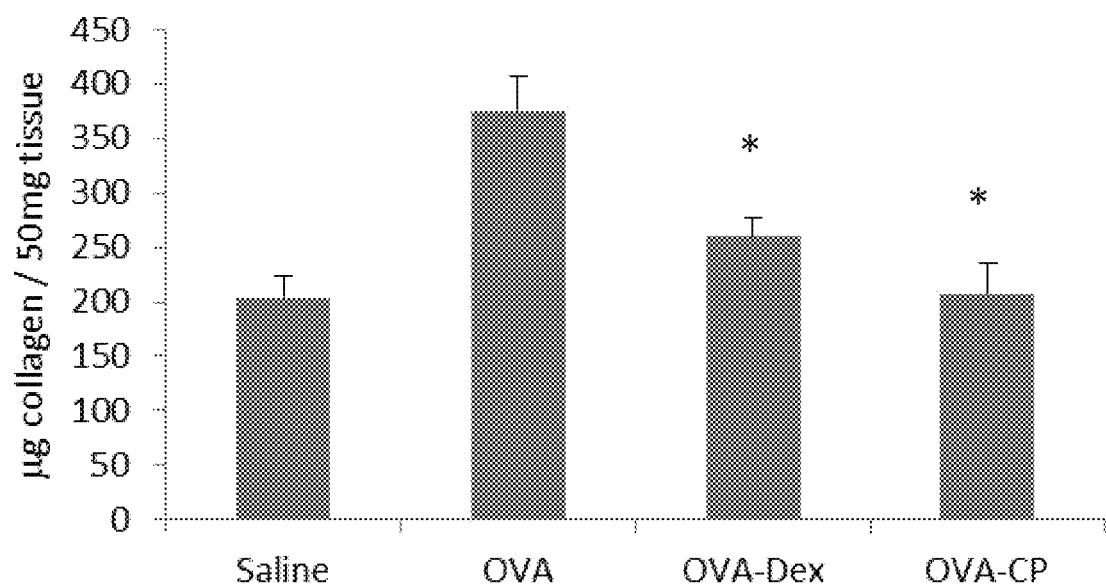

FIG. 16 is a bar graph showing collagen concentration in lung tissue from mice treated for 4 weeks with ovalbumin alone (OVA) or ovalbumin with dexamethasone (OVA-Dex) or 3-CP (OVA-CP), or with saline (*p<0.05 vs. OVA).

Figure 17:
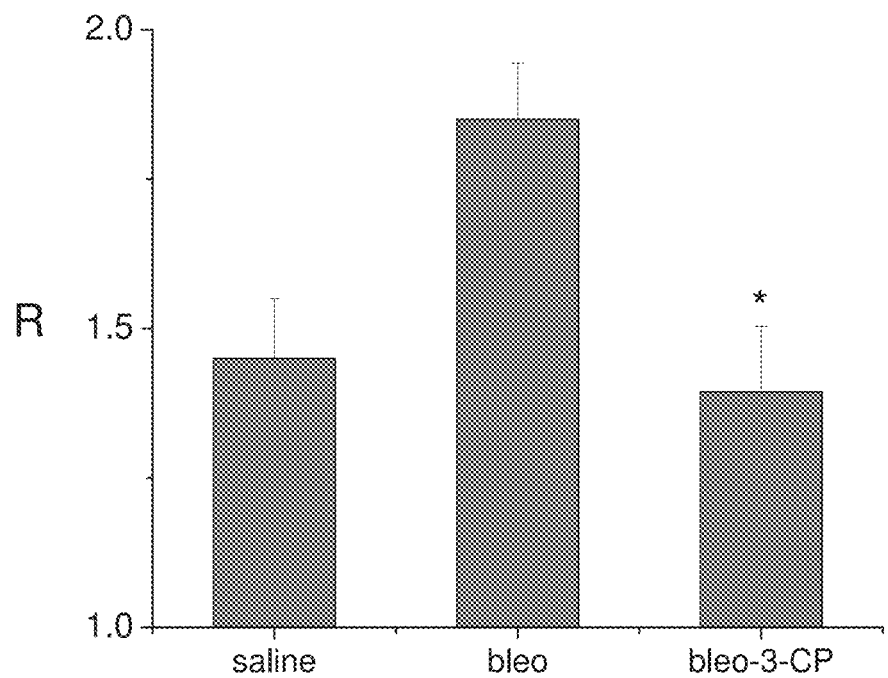

FIG. 17 is a bar graph showing lung resistance (R) in mice in response to administration of 64 mg/ml methacholine, following treatment with bleomycin (bleo), bleomycin with 3-CP (belo-3-CP), or saline (*p=0.01 relative to bleo).

Figure 18:
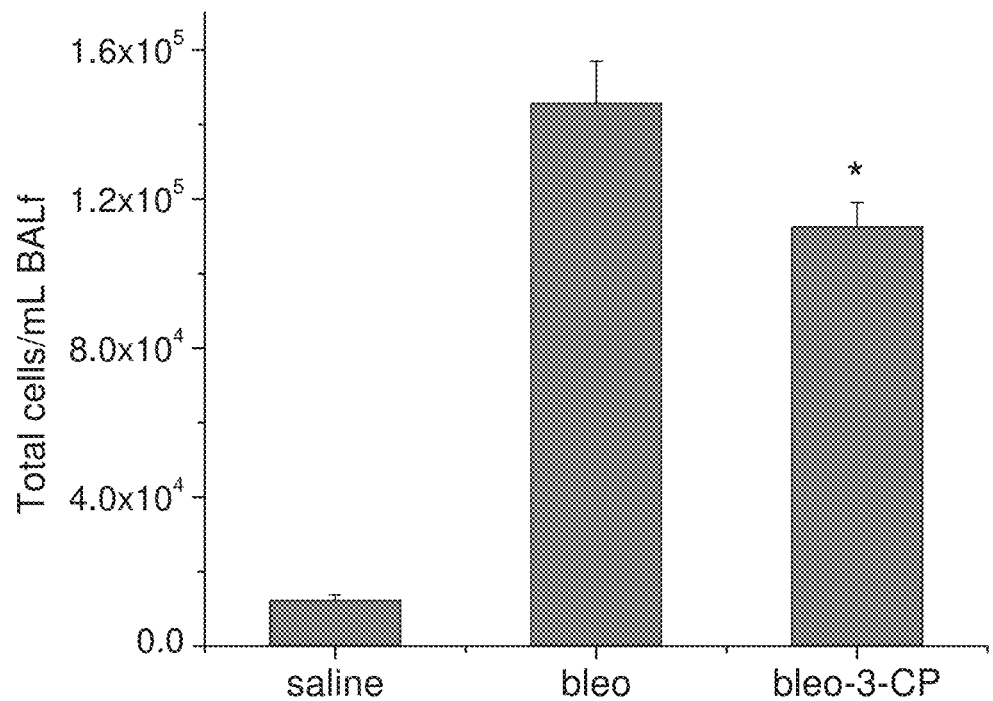

FIG. 18 is a bar graph showing total inflammatory cells per ml of bronchoalveolar lavage (BAL) fluid from mice treated with bleomycin alone (bleo) or with 3-CP (bleo-3-CP), and from control mice treated with saline (*p=0.023 relative to bleo).

Figure 19:
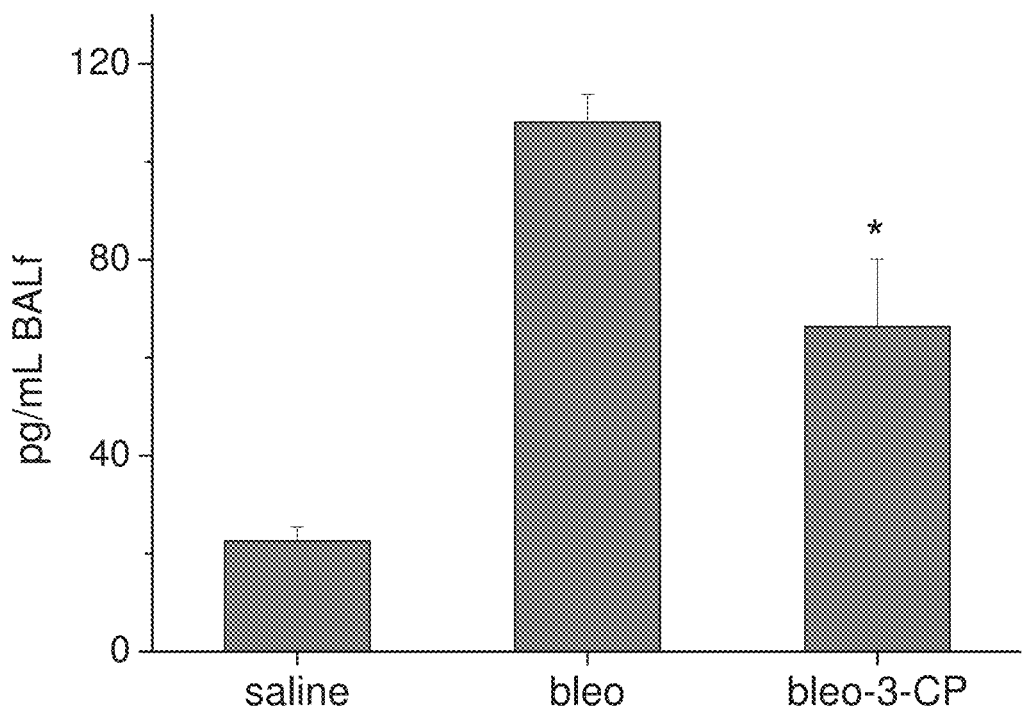

FIG. 19 is a bar graph showing the concentration of TGF-β1 in bronchoalveolar lavage (BAL) fluid from mice treated with bleomycin alone (bleo) or with 3-CP (bleo-3-CP), and from control mice treated with saline (*p<0.05 relative to bleo).

Figure 20:
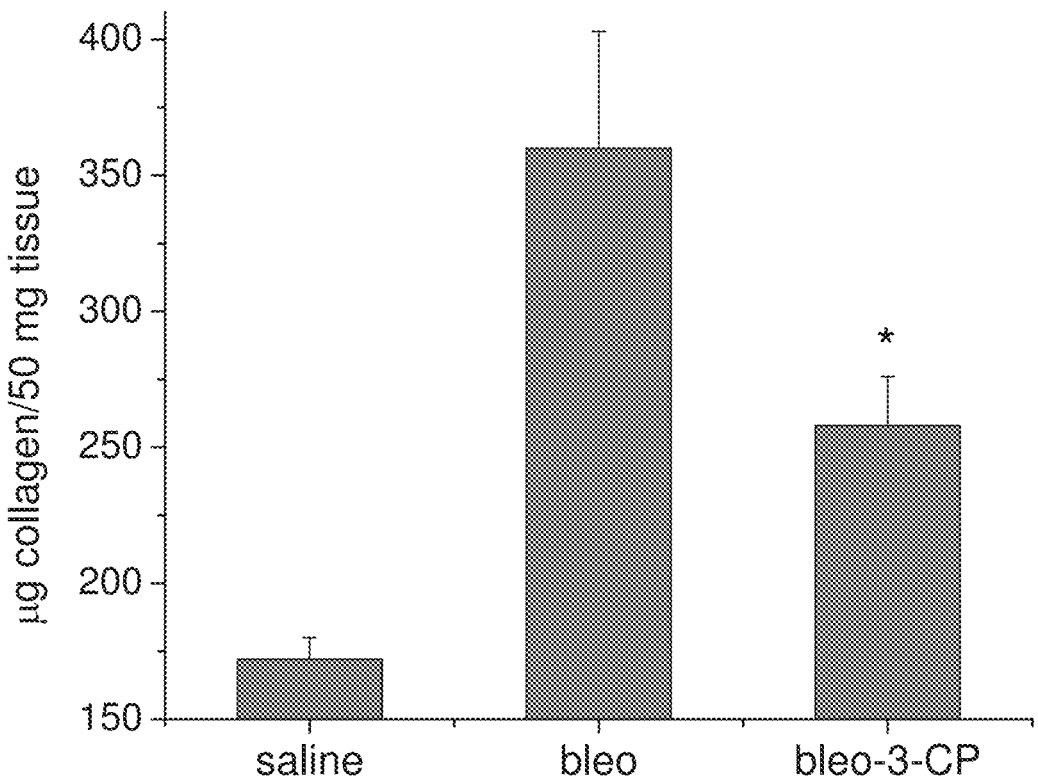

FIG. 20 is a bar graph showing collagen concentration in lung tissue from mice treated with bleomycin alone (bleo) or with 3-CP (bleo-3-CP), and from control mice treated with saline (*p<0.05 relative to bleo).

DESCRIPTION OF SPECIFIC EMBODIMENTS OF THE INVENTION

The present invention, in some embodiments thereof, relates to therapy, and more particularly, but not exclusively, to treatment of diseases and disorders of the respiratory tract using nitroxide radicals.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While studying biological effects of cyclic nitroxides, the present inventors have uncovered that cyclic nitroxides with 5-membered rings are highly effective at inhibiting development and progression of diseases of the respiratory tract.

The present inventors have further uncovered that cyclic nitroxides are surprisingly effective at inhibiting remodeling of respiratory tract tissue in response to different pathologies. Such inhibition of remodeling has not been reported for other compounds reported to have antioxidant activity.

Figure 1:
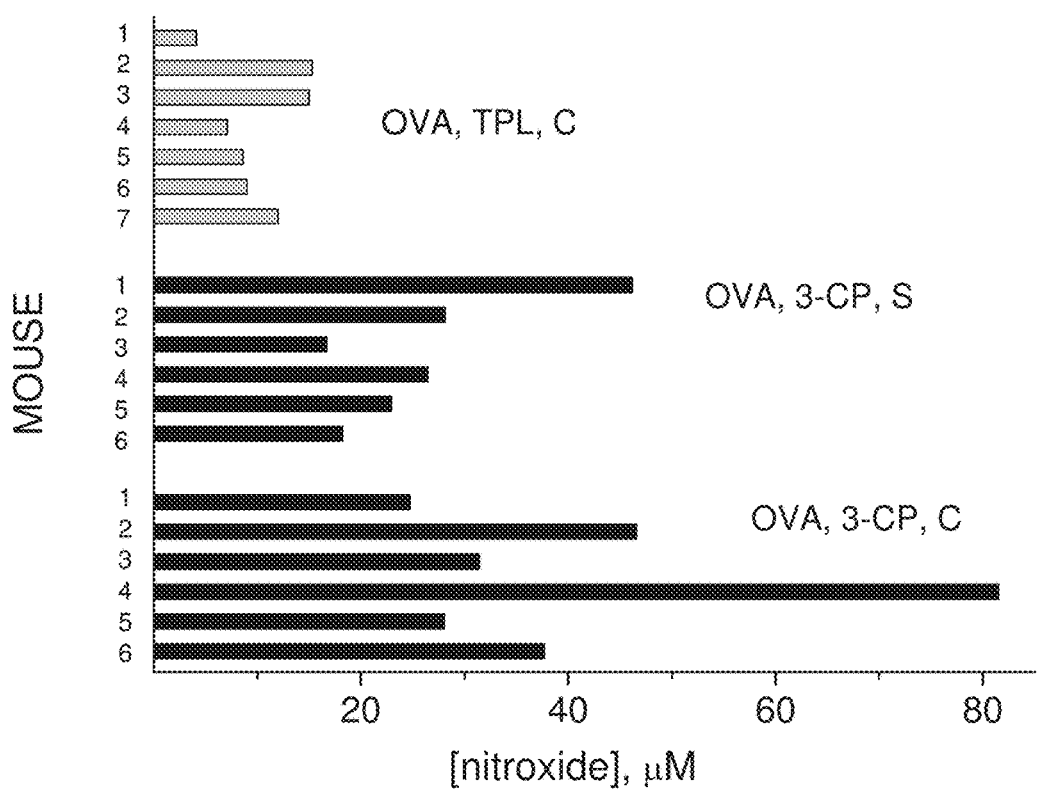

Referring now to the drawings, FIG. 1 shows that nitroxides are present in blood upon oral administration, and that the nitroxide 3-CP (which has a 5-membered ring) is present in the blood in higher proportions than the nitroxide Tempol (which has a six-membered ring). FIG. 12 shows that the nitroxide 3-CPT (which has a 5-membered ring) is also present in blood upon oral administration.

Figure 2:
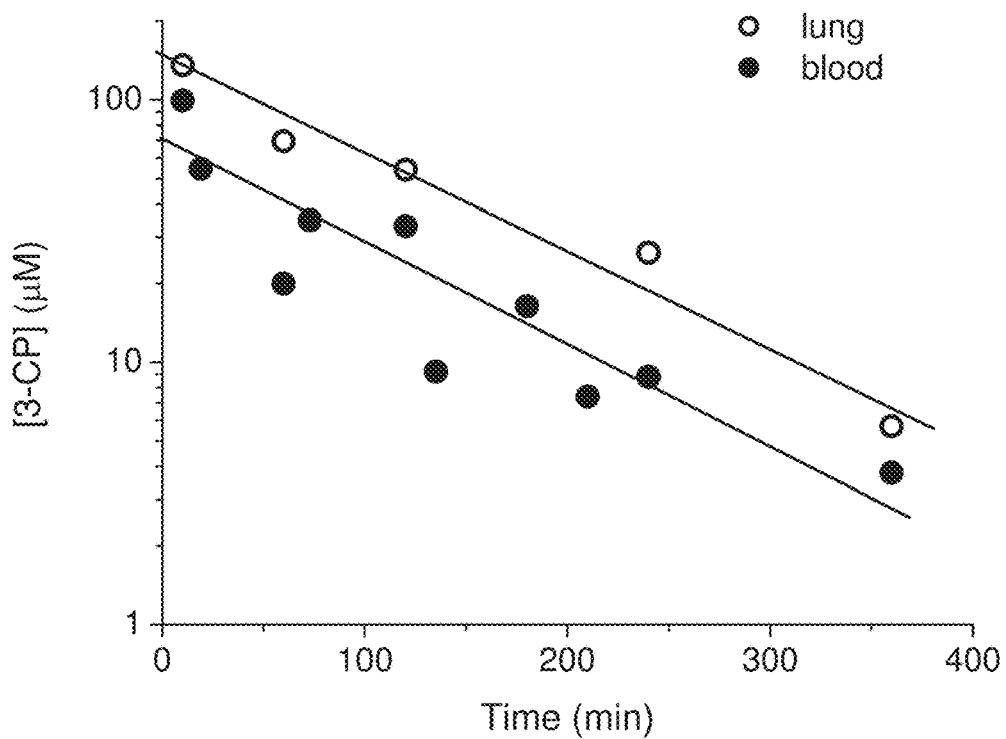

FIG. 2 shows that administered 3-CP is present in lung tissue at higher concentrations than in the blood.

FIGS. 3-4 show that 3-CP is considerably more effective than Tempol at reducing lung resistance and inflammatory cell levels (especially eosinophil levels) in asthmatic animals.

FIGS. 5-7E show that 3-CP is effective upon oral, intraperitoneal or intranasal administration, in inhibiting increases in inflammatory cell levels and lung resistance, as well as changes in cytokine levels, in asthmatic animals. FIGS. 9-11 show that 3-CP upon oral, intraperitoneal or intranasal administration protects against lung pathology in asthmatic animals. FIG. 13 shows that 3-CPT is also effective upon oral or intraperitoneal administration in inhibiting increases in inflammatory cell levels (especially eosinophil levels) in asthmatic animals. FIG. 14 shows that 3-CP is more effective than 3-CPT in reducing lung resistance.

FIG. 8 shows that 3-CP is effective at inhibiting nitrotyrosine production in asthmatic animals, whereas dexamethasone is not.

FIGS. 15A-15B show that 3-CP is effective at reducing inflammatory cell levels (especially eosinophil levels) in severe (chronic) asthma. FIGS. 17-19 show that CP is effective at reducing lung resistance, inflammatory cell levels and pro-inflammatory cytokine levels in pulmonary fibrosis. FIGS. 16 and 20 show that 3-CP reverses airway remodeling in both severe (chronic) asthma and pulmonary fibrosis.

According to an aspect of some embodiments of the invention, there is provided a cyclic nitroxide compound for use in treating a disease or disorder of the respiratory tract.

Cyclic nitroxide compounds, diseases and disorders of the respiratory tract, and treatments thereof, which may be included in embodiments according to any of the aspects of the invention described herein, are described in detail hereinafter.

According to an aspect of some embodiments of the invention, there is provided a use of a cyclic nitroxide compound in the manufacture of a medicament for treating a disease or disorder of the respiratory tract.

According to an aspect of some embodiments of the invention, there is provided a method of treating a disease or disorder of the respiratory tract, the method comprising administering to a subject in need thereof a cyclic nitroxide compound.

Cyclic Nitroxides:

As used herein, the term "nitroxide" refers to a non-electrically charged functional group comprising a nitrogen atom which is covalently bound to three atoms via saturated covalent bonds, wherein one of said three atoms is an oxygen radical (—O.) covalently bound only to the nitrogen atom, or to a compound comprising such a functional group. Such a functional group or compound is typically regarded as a free radical, which may be depicted as $R_xR_yN$—O., wherein $R_x$ and $R_y$ are each independently a substituted or unsubstituted hydrocarbon moiety, optionally linked hydrocarbon moieties.

As used herein, the term "cyclic nitroxide" refers to a compound comprising a nitroxide functional group (as defined herein), wherein the nitrogen atom of the nitroxide group forms a part of a ring (e.g., a heteroalicyclic ring). Such a functional group or compound is typically regarded as a free radical, which may be depicted as $R_xR_yN$—O., wherein $R_x$ and $R_y$ form together a ring, for example, a 5-membered, 6-membered or 7-membered heterocyclic ring, which may be saturated or unsaturated, and is preferably non-aromatic.

In some embodiments of any of the embodiments described herein, the cyclic nitroxide compound has the general formula II:

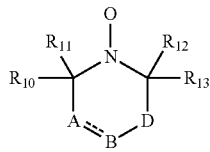

Formula II wherein:

the dashed line denotes a saturated bond or unsaturated bond;

$R_{10}$-$R_{13}$ are each independently a $C_{1-4}$-alkyl, or alternatively, $R_{10}$ and $R_{11}$, and/or $R_{12}$ and $R_{13}$, together form a 3-7-membered alicyclic ring;

A is $CR_{14}R_{15}$, C=O, O, S or $NR_{16}$ when the dashed line denotes a saturated bond, and is $CR_{17}$ or N when the dashed line denotes an unsaturated bond;

B is $CR_{18}R_{19}$, C=O, O, S or $NR_{20}$ when the dashed line denotes a saturated bond, and is $CR_{21}$ or N when the dashed line denotes an unsaturated bond;

D is $CR_{21}R_{22}$, C=O, O, S or $NR_{23}$, such that the compound comprises a six-membered cyclic nitroxide ring, or alternatively, D is absent such that B is directly attached to a carbon atom adjacent to the nitroxide nitrogen atom, forming a five-membered cyclic nitroxide ring; and $R_{14}$-$R_{23}$ are each independently hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine or amino, or alternatively, any one of $R_{18}$-$R_{20}$ and any one of $R_{14}$-$R_{16}$ and $R_{21}$-$R_{23}$ together form an aromatic (aryl or heteroaryl), alicyclic or heteroalicyclic ring, which may be substituted or unsubstituted.

In some embodiments of any of the embodiments described herein, A is $CR_{14}R_{15}$ or C=O. In some embodiments, A is $CR_{14}R_{15}$.

In some embodiments of any of the embodiments described herein, B is $CR_{18}R_{19}$ or C=O. In some embodiments, B is $CR_{18}R_{19}$.

In some embodiments of any of the embodiments described herein, A is $CR_{14}R_{15}$ or C=O, and B is $CR_{18}R_{19}$ or C=O.

In some embodiments of any of the embodiments described herein, at least one of $R_{14}$-$R_{23}$ is a substituent which increased water-solubility (e.g., at pH 7, 25° C.) of the compound in comparison with a corresponding compound having hydrogen at the same position (e.g., wherein $R_{14}$-$R_{23}$ are each hydrogen).

In some embodiments of any of the embodiments described herein, $R_{14}$-$R_{23}$ are each independently hydrogen, alkyl (optionally alkyl substituted by hydroxy, amino or C-carboxy), hydroxy, alkoxy, C-amido (optionally —C(=O)NH$_2$), N-amido (optionally acetamido), C-carboxy (optionally —C(=O)OH), or amino (optionally —NH$_2$). In some embodiments, $R_{14}$-$R_{23}$ are each independently hydrogen, hydroxy or C-amido.

In some embodiments of any of the embodiments described herein wherein any one of $R_{18}$-$R_{20}$ and any one of $R_{14}$-$R_{16}$ and $R_{21}$-$R_{23}$ together form an aromatic, alicyclic or heteroalicyclic ring. The ring is aromatic (e.g., a substituted or unsubstituted benzene ring) when the dashed line denotes an unsaturated bond, and is alicyclic or heteroalicyclic when the dashed line denotes a saturated bond.

In some embodiments of any of the embodiments described herein, at least one of $R_{14}$-$R_{23}$ is not hydrogen and/or at least one of A, B and D is C=O or O. In some embodiments, one or more of $R_{14}$, $R_{15}$, $R_{18}$, $R_{19}$, $R_{21}$ and $R_{22}$ is not hydrogen. In some embodiments, one or more of $R_{14}$, $R_{15}$, $R_{18}$, $R_{19}$, $R_{21}$ and $R_{22}$ is C-amido or hydroxy. In some such embodiments, $R_{18}$ is not hydrogen. In some embodiments, $R_{18}$ is C-amido or hydroxy.

In some embodiments of any of the embodiments described herein, $R_{14}$-$R_{17}$ and $R_{19}$-$R_{23}$ are each hydrogen.

In some embodiments of any of the embodiments described herein, one or more, or each, of $R_{10}$-$R_{13}$ are unsubstituted alkyl and/or $R_{10}$ and $R_{11}$ and/or $R_{12}$ and $R_{13}$ form an unsubstituted 3-7-membered alicyclic ring. In some embodiments, one or more, or each, of $R_{10}$-$R_{13}$ are independently methyl, ethyl or propyl. In some embodiments, one or more, or each, of $R_{10}$-$R_{13}$ are methyl.

In some embodiments of any of the embodiments described herein, D is not absent. 4-Hydroxy-2,2,6,6-tetramethyl-piperidin-1-oxyl (Tempol) is a non-limiting example of a cyclic nitroxide wherein D is not absent (e.g., wherein D is CH$_2$).

In some embodiments of any of the embodiments described herein, D is absent. 3-Carbamoyl-2,2,5,5-tetramethyl-pyrrolidin-1-oxyl (3-CP) and 3-carbamoyl-2,2,5,5-tetramethyl-3-pyrrolin-1-oxyl (3-CPT) are non-limiting examples of cyclic nitroxides wherein D is absent.

In some embodiments of any of the embodiments described herein wherein D is absent, the cyclic nitroxide compound has the general formula I:

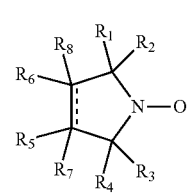

Formula I wherein:

the dashed line denotes a saturated bond or unsaturated bond, wherein when the dashed line denotes an unsaturated bond, $R_7$ and $R_8$ are absent;

$R_1$-$R_4$ are as defined herein for $R_{10}$-$R_{13}$, respectively, according to any of the respective embodiments described herein; and $R_5$-$R_8$ are each hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine or amino (or dashed line denotes an unsaturated bond and $R_7$ and $R_8$ are absent, as described hereinabove).

In some embodiments of any of the embodiments described herein, at least one of $R_5$-$R_8$ is a substituent which increased water-solubility (e.g., at pH 7, 25° C.) of the compound in comparison with a corresponding compound having hydrogen at the same position (e.g., wherein $R_5$-$R_8$ are each hydrogen).

In some embodiments of any of the embodiments described herein, $R_5$-$R_8$ are each independently hydrogen, alkyl (optionally alkyl substituted by hydroxy, amino or C-carboxy), hydroxy, alkoxy, C-amido (optionally —C(=O)NH$_2$), N-amido (optionally acetamido), C-carboxy (optionally —C(=O)OH), or amino (optionally —NH$_2$). In some embodiments, $R_5$-$R_8$ are each independently hydrogen, hydroxy or C-amido.

In some embodiments of any of the embodiments described herein, at least one of $R_5$-$R_8$ is neither hydrogen nor absent. In some such embodiments, $R_5$ is not hydrogen. In some embodiments of any of the embodiments described herein, at least one of $R_5$-$R_8$ is C-amido, optionally —C(=O)NH$_2$. In some embodiments, $R_5$ is C-amido, optionally —C(=O)NH$_2$.

In some embodiments of any of the embodiments described herein, $R_6$ is hydrogen, and each of $R_7$ and $R_8$ is either hydrogen or absent.

In some embodiments of any of the embodiments described herein, the dashed line denotes a saturated bond. 3-Carbamoyl-2,2,5,5-tetramethyl-pyrrolidin-1-oxyl is a non-limiting example of a compound having Formula I wherein the dashed line denotes a saturated bond.

As exemplified in the Examples section herein, compounds having Formula I, and especially compounds having Formula I wherein the dashed line denotes a saturated bond, are particularly effective at treating respiratory diseases or disorders.

In some embodiments of any of the embodiments described herein, the compound does not comprise a NSAID moiety, for example, none of the substituents of the compound (e.g., $R_1$-$R_8$ in Formula I and/or $R_{10}$-$R_{23}$ in Formula II) is or comprises a NSAID (non-steroidal anti-inflammatory drug) moiety.

Herein, the term "NSAID moiety" refers to a moiety in a compound which corresponds to a NSAID known in the art upon conjugation to another moiety, for example, upon linking the NSAID directly or indirectly to a cyclic nitroxide. The compound may optionally be in a form of a NSAID with at least one attached substituent (e.g., a cyclic nitroxide-containing substituent) and/or the NSAID moiety is attached via a cleavable bond (e.g., ester bond, amide bond), wherein cleavage of the bond results in formation of a NSAID. The term "NSAID moiety" can be regarded as referring to a major portion of an NSAID (e.g., an NSAID lacking one or more atoms or groups due to conjugation).

Examples of NSAID moieties according to some embodiments described herein, without limitation, moieties of aspirin (e.g., acetylsalicoyl), salicylate (e.g., salicoyl, 2-carboxyphenoxy), salsalate (e.g., 2-(2-hydroxybenzoyl)oxybenzoyl, 2-((2-carboxyphenoxy)carbonyl)phenoxy), diflunisal (e.g., 2',4'-difluoro-4-hydroxybiphenyl-3-carbonyl, 2',4'-difluoro-3-carboxy-biphenyl-4-oxy), ibuprofen (e.g., 2-(4-(2-methylpropyl)phenyl)propanoyl), naproxen (e.g., 2-(6-methoxynaphthalen-2-yl)propanoyl), fenoprofen (e.g., 2-(3-phenoxyphenyl)propanoyl), ketoprofen (e.g., 2-(3-benzoylphenyl)propanoyl), flurbiprofen (e.g., 2-(2-fluorobiphenyl-4-yl)propanoyl), oxaprozin (e.g., 3-(4,5-diphenyl-1,3-oxazol-2-yl)propanoyl), loxoprofen (e.g., 2-(4-((2-oxocyclopentyl)methyl)phenyl)propanoyl), indomethacin (e.g., 2-(1-((4-chlorophenyl)carbonyl)-5-methoxy-2-methyl-1H-indol-3-yl)acetyl, sulindac (e.g., ((1Z)-5-fluoro-2-methyl-1-(4-methylsulfinyl)benzylidene)-1H-indene-3-yl)acetyl), etodolac (e.g., 2-(1,8-diethyl-4,9-dihydro-3H-pyrano[3,4-b]indol-1-yl)acetyl), diclofenac (e.g., 2-(2,6-dichloroanilino)phenylacetyl), aceclofenac (e.g., 2-(2-(2-((2,6-dichlorophenyl)amino)phenyl)acetyl) oxyacetyl), tolmetin (e.g., (1-methyl-5-(4-methylbenzoyl)-1H-pyrrol-2-yl)acetyl), ketorolac (e.g., 5-benzoyl-2,3-dihydro-1H-pyrrolizine-1-carbonyl), nabumetone (e.g., 4-(6-methoxy-2-naphthyl)-2-oxo-butyl), piroxicam (e.g., a 4-hydroxy-2-methyl-N-(2-pyridinyl)-2H-1,2-benzothiazine-3-carboxamide-1,1-dioxide moiety), meloxicam (e.g., a 4-hydroxy-2-methyl-N-(5-methyl-2-thiazolyl)-2H-1,2-benzothiazine-3-carboxamide 1,1-dioxide moiety), tenoxicam (e.g., a 3-(hydroxy(pyridin-2-ylamino)methylene)-2-methyl-2,3-dihydro-4H-thieno[2,3-e]thiazin-4-one-1,1-dioxide moiety), droxicam, lornoxicam (e.g., a 6-chloro-3-(hydroxyl(pyridine-2-ylamino)methylene)-2-methyl-2,3-dihydro-4H-thieno [2,3-e][1,2]thiazin-4-one-1,1-dioxide moiety), isoxicam, mefenamic acid (e.g., 2-(2,3-dimethylphenyl)aminobenzoyl), meclofenamic acid (e.g., 2-((2,6-dichloro-3-methylphenyl)amino)benzoyl), flufenamic acid (e.g., 2-((3-trifluoromethyl)phenyl)amino)benzoyl), tolfenamic acid (e.g., 2-((3-chloro20methylphenyl)amino)benzoyl), celecoxib (e.g., 4-(5-(4-methylphenyl)-3-(trifluoromethyl)pyrazol-1-yl)benzenesulfonamido), rofecoxib (e.g., a 4-(4-methylsulfonylphenyl)-3-phenyl-5H-furan-2-one moiety), valdecoxib (e.g., 4-(5-methyl-3-phenylisoxazol-4-yl) benzenesulfonamido), parecoxib, lumiracoxib (e.g., (2-((2-chloro-6-fluorophenyl)amino)-5-methylphenyl)acetyl), etoricoxib (e.g., a 5-chloro-6'-methyl-3-(4-(methylsulfonyl) phenyl)-2,3'-bipyridine moiety), nimesulide (e.g., a N-(4-nitro-2-phenoxyphenyl)methanesulfonamido moiety), niflumic acid (e.g., 2-((3-(trifluoromethyl)phenyl)amino) nicotinoyl), licofenac, licofelone (e.g., (6-(4-chlorophenyl)-2,2-dimethyl-7-phenyl-2,3-dihydro-1H-pyrrolizin-5-yl) acetyl), and clonixin (e.g., 2-(3-chloro-2-methylanilino) pyridine-3-carbonyl).

Further examples of NSAID moieties according to some embodiments are described in U.S. Patent Application Publication No. 2012/0263650, the contents of which are incorporated herein in their entirety, particularly contents relating to NSAID moieties attachable to a nitroxide.

A NSAID moiety may optionally be formed by conjugation of a carboxy or hydroxy group of the NSAID (optionally a NSAID listed hereinabove) via an ester bond or conjugation of a carboxy group or nitrogen atom (e.g., an amine group nitrogen atom) of the NSAID (optionally a NSAID listed hereinabove) via an amide bond. Alternatively or additionally, a NSAID moiety may optionally be formed by substituting a hydrogen atom in a NSAID molecule optionally a NSAID listed hereinabove) with a moiety being conjugated to the NSAID moiety (e.g., a cyclic nitroxide moiety or a linker attached to a cyclic nitroxide moiety).

Herein, the term "hydrocarbon" describes an organic moiety that includes, as its basic skeleton, a chain of carbon atoms (optionally one carbon atom), substituted mainly by hydrogen atoms. The hydrocarbon can be saturated or non-saturated, be comprised of aliphatic, alicyclic or aromatic moieties, and can optionally be substituted by one or more substituents (other than hydrogen). A substituted hydrocarbon may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine. The hydrocarbon moiety is optionally interrupted by one or more heteroatoms, including, without limitation, one or more oxygen, nitrogen and/or sulfur atoms. In some embodiments of any of the embodiments described herein relating to a hydrocarbon, the hydrocarbon is not interrupted by any heteroatoms.

Preferably, the hydrocarbon moiety has 1 to 20 carbon atoms. Whenever a numerical range; e.g., "1 to 20", is stated herein, it implies that the group, in this case the alkyl group, may contain 1 carbon atom, 2 carbon atoms, 3 carbon atoms, etc., up to and including 20 carbon atoms.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

An "alkenyl" group refers to an unsaturated group corresponding to an alkyl group (as defined herein) which consists of at least two carbon atoms and at least one carbon-carbon double bond.

An "alkynyl" group refers to an unsaturated group corresponding to an alkyl group (as defined herein) which consists of at least two carbon atoms and at least one carbon-carbon triple bond.

A "cycloalkyl" group refers to an all-carbon monocyclic or fused ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

An "aryl" or "aromatic" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroaryl" or "heteroaromatic" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted.

When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein. Representative examples are piperidine, piperazine, tetrahydrofuran, tetrahydropyran, morpholine and the like.

As used herein, the terms "amine" and "amino" refer to either a —NR'R" group or a —N$^+$R'R"R"' group, wherein R, R" and R"' are each independently hydrogen, alkyl, alkenyl, alkynyl, cycloalkyl, heteroalicyclic (bonded through a ring carbon), aryl and heteroaryl (bonded through a ring carbon). Optionally, R', R" and R"' are each independently hydrogen or alkyl comprising 1 to 4 carbon atoms. Optionally, R' and R" are hydrogen.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is defined as hereinabove.

A "thiocarbonyl" group refers to a —C(=S)—R' group, where R' is as defined herein.

A "C-carboxy" group refers to a —C(=O)—O—R' groups, where R' is as defined herein.

An "O-carboxy" group refers to an R'C(=O)—O— group, where R' is as defined herein.

A "carboxy" or "carboxyl" encompasses both C-carboxy and O-carboxy groups, as defined herein.

A "carboxylic acid" group refers to a carboxy group wherein R' is hydrogen.

An "ester" group refers to a carboxy group wherein R' is not hydrogen.

An "ester bond" refers to a carbon-oxygen single bond of an ester group.

An "oxo" group refers to a =O group.

A "halo" group refers to a fluorine, chlorine, bromine or iodine atom.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamide" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR"— group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

An "amide bond" refers to a carbon-nitrogen bond in an amide group.

A "urea" group refers to an —N(R')—C(=O)—NR"R'" group, where each of R', R" and R'" is as defined herein.

The term "thiourea" describes a —N(R')—C(=S)—NR"— group, with each of R' and R" as defined hereinabove.

A "nitro" group refers to an —NO$_2$ group.

An "azide" group refers to a —N=N$^+$=N$^-$ group.

A "cyano" or "nitrile" group refers to a —C≡N group.

The term "hydrazine" describes a —N(R')—N(R")R'" group, with each of R', R" and R'" as defined hereinabove.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

Respiratory Tract Conditions:

Herein, the phrase "respiratory tract" refers to organs, tissues and airways involved in respiration, and encompasses the upper respiratory tract (including nasal passages, paranasal sinuses, pharynx, the portion of the larynx above the vocal chords) and lower respiratory tract (including the portion of the larynx below the vocal chords, trachea, bronchi, bronchioles and lungs).

The diseases or disorders of the respiratory tract which may be treated by embodiments of the invention include any disease or disorder afflicting (at least) the upper respiratory tract (as defined herein) and/or lower respiratory tract (as defined herein).

In some embodiments of any of the embodiments described herein, the disease or disorder of the respiratory tract afflicts at least the lower respiratory tract.

In some embodiments of any of the embodiments described herein, the disease or disorder is a lung disease or disorder.

Herein, the phrase "lung disease or disorder" encompasses diseases and disorders which afflict bronchi, bronchioles and/or the lung per se (e.g., respiratory bronchioles, alveolar ducts, alveolar sacs and/or alveoli), and encompasses, for example, obstructive lung diseases and disorders and an interstitial lung diseases and disorders.

In some embodiments, the lung disease or disorder afflicts (at least) the lung per se (e.g., respiratory bronchioles, alveolar ducts, alveolar sacs and/or alveoli).

Herein, the phrase "obstructive lung disease or disorder" refers to diseases or disorders characterized by obstruction of a lung airway, for example, by narrowing of bronchi and/or bronchioles.

Examples of obstructive lung diseases and disorders which may be treated according to some embodiments of the invention include, without limitation, asthma, bronchitis (including, for example, acute bronchitis, chronic bronchitis and bronchiolitis), bronchiectasis, and chronic obstructive pulmonary disease (COPD).

Herein, the phrase "interstitial lung disease or disorder" refers to diseases or disorders afflicting interstitium of a lung (tissue and space around air sacs of a lung), for example, alveolar epithelium, pulmonary capillary endothelium, basement membrane, perivascular tissue and/or perilymphatic tissue.

Examples of interstitial lung diseases and disorders which may be treated according to some embodiments of the invention include, without limitation, pulmonary fibrosis (including, for example, idiopathic pulmonary fibrosis and autoimmune-related pulmonary fibrosis); interstitial lung diseases and disorders associated with inhaled substances, such as hypersensitivity pneumonitis and pneumoconiosis (including coalworker's pneumoconiosis, asbestosis, silicosis, bauxite fibrosis, berylliosis, siderosis, byssinosis, silicosiderosis, Labrador lung, and/or stannosis); infectious interstitial lung diseases, such as atypical pneumonia, pneumocystis pneumonia, tuberculosis, *Chlamydia trachomatis* and/or respiratory syncytial virus infection; drug-induced interstitial lung diseases, such as antibiotic-induced, chemotherapy-induced, antiarrhythmic agent-induced and/or statin-induced interstitial lung disease; interstitial lung diseases associated with a connective tissue disease, such as systemic sclerosis/scleroderma, polymyositis, dermatomyositis, systemic lupus erythematosus and/or rheumatoid arthritis; sarcoidosis; acute interstitial pneumonia; idiopathic interstitial pneumonia; anti-synthetase syndrome; and granulomatosis with polyangiitis.

Herein, the term "asthma" refers to a chronic inflammatory disease or disorder of airways, characterized by recurrent episodes of wheezing, coughing, chest tightness and/or shortness of breath. The term "chronic asthma" refers to irreversible effects such as remodeling which may occur following long-term affliction with asthma.

Herein, the term "bronchitis" refers to inflammation of bronchi (and/or bronchioles), and encompasses acute bronchitis (which commonly results in coughing for up to several weeks), chronic bronchitis (e.g., productive cough lasting at least three months per year for at least two years), and bronchiolitis (inflammation of bronchioles).

Herein, the term "bronchiectasis" refers to permanent enlargement of at least a portion of lung airways.

Herein, the terms "chronic obstructive pulmonary disease" and "COPD" refer to an obstructive lung disease characterized by long-term poor airflow (which may be determined according to standard lung function tests used in the art), with common symptoms including shortness of breath and cough with sputum production.

Herein, the term "pulmonary fibrosis" refers to scar formation in lung tissue, which may lead to breathing problems. Typically, pulmonary fibrosis leads to thickening of lung tissue walls, impairing supply of oxygen to the body, which can cause perpetual shortness of breath. Pulmonary fibrosis may be identified as being a secondary effect of another disease or disorder (e.g., an interstitial lung disease or disorder described herein), or alternatively, may have no identified cause (in which case it is also referred to as "idiopathic pulmonary fibrosis"). The phrase "autoimmune-related pulmonary fibrosis" refers to pulmonary fibrosis identified as being a secondary effect of an autoimmune disease or disorder (e.g., an autoimmune disease or disorder described herein).

Herein, the phrase "interstitial lung diseases and disorders associated with inhaled substances" refers to interstitial lung diseases and disorders (e.g., including inflammation of alveoli), as defined herein, caused by inhalation of certain substances, such as an organic and/or inorganic dust. Such lung diseases and disorders may (but do not necessarily) result in pulmonary fibrosis upon prolonged exposure to the inhaled substance. The term "pneumoconiosis" refers to interstitial lung diseases and disorders associated with inhaled inorganic substances. The term "hypersensitivity pneumonitis" refers to interstitial lung diseases and disorders associated with inhaled organic substances, and includes acute, subacute and chronic hypersensitivity pneumonitis.

Herein, the phrase "infectious interstitial lung diseases" refers to interstitial lung diseases and disorders, as defined herein, which are caused by infection by a virus, bacterium and/or other microorganism (e.g., fungi, protozoa). Such lung diseases and disorders may (but do not necessarily) result in pulmonary fibrosis upon prolonged infection.

Herein, the phrase "drug-induced interstitial lung diseases" refers to interstitial lung diseases and disorders, as defined herein, which are identified as a side effect of a drug (e.g., a drug described herein). Such lung diseases and disorders may (but do not necessarily) result in pulmonary fibrosis.

Examples of drugs which may induce drug-induced interstitial lung disease (according to any of the respective embodiments described herein) include, without limitation, amiodarone, bleomycin, pingyangmycin, busulfan, methotrexate, apomorphine and nitrofurantoin.

Herein, the phrase "connective tissue disease" refers to a disease in which connective tissue (e.g., extracellular matrix, collagen and/or elastin) is a target of pathology. A connective tissue disease may be (but is not necessarily) caused by an autoimmune reaction against the connective tissue and/or by a hereditary defect and/or abnormal growth of connective tissue.

Herein, the phrase "interstitial lung diseases associated with a connective tissue disease" encompasses interstitial lung diseases and disorders in which a connective tissue disease in a given subject primarily targets connective tissue in lung, as well as any interstitial lung disease or disorder (e.g., damage to ling tissue) which represents one manifestation of a connective tissue disease (as defined herein), which may affect many other regions of the body in the same subject (e.g., as is common in systemic scleroderma/scleroderma, polymyositis, dermatomyositis, rheumatoid arthritis, or systemic lupus erythematosus).

Herein, the term "sarcoidosis" refers to a disease involving abnormal collections of inflammatory cells (granulomas) that can form as nodules in multiple organs, frequently in lungs or associated lymph nodes.

Herein, the term "anti-synthetase syndrome" encompasses a presence of antibodies targeting tRNA synthetase enzymes in a subject exhibiting clinical features of interstitial lung disease or disorder (as defined herein).

Herein, the phrase "granulomatosis with polyangiitis" refers to a systemic disorder involving both granulomas (a collection of immune cells) and polyangiitis (inflammation of multiple blood vessels or lymph vessels). Potential manifestations of the condition in lungs include, without limitation, pulmonary nodules, infiltrates, cavitary lesions, pulmonary hemorrhage causing hemoptysis, and/or bronchial stenosis.

In some embodiments of any of the embodiments described herein, the disease or disorder of the respiratory tract is an inflammatory disease or disorder of the respiratory tract. In some embodiments, the inflammatory disease or disorder is an inflammatory lung disease or disorder (as defined herein).

Herein, the term "inflammatory" encompasses swelling of a tissue and/or increased levels of immune cells in the tissue (e.g., afflicting a tissue of the respiratory tract), which may be acute and/or chronic.

Examples of inflammatory diseases and disorders include, without limitation, diseases/disorders associated with a hypersensitivity reaction, including type I hypersensitivity (allergy, e.g., asthma), type II hypersensitivity, type III hypersensitivity (e.g., rheumatoid arthritis, systemic lupus erythematosus, hypersensitivity pneumonitis), type IV hypersensitivity and/or type V hypersensitivity, as these terms are used in the art; airway hyper-responsiveness (AHR) (e.g., enhanced sensitivity to methacholine and/or histamine in a bronchial challenge test); reversible airflow obstruction; increased numbers of eosinophils, mast cells and/or lymphocytes (e.g., in afflicted respiratory tract tissue); and/or increased release of pro-inflammatory cytokines (e.g., in afflicted respiratory tract tissue).

In some embodiments relating to inflammatory diseases or disorders of the respiratory tract, the disease or disorder is associated with increased release of one or more of the pro-inflammatory cytokines interleukin-4 (IL-4), interleukin-5 (IL-5), interleukin-13 (IL-13), and a transforming growth factor-$\beta$ (TGF-$\beta$), optionally TGF-$\beta$1.

In some embodiments of any of the embodiments described herein, the disease or disorder of the respiratory tract is associated with respiratory tract remodeling. In some such embodiments, the treatment interferes with and/or reduces a rate and/or degree of respiratory tract remodeling.

As used herein and in the art, the term "remodeling" refers to long-term (e.g., irreversible) structural changes in tissue (e.g., tissue of the respiratory tract) which are not observed in a healthy subject.

In some of any of the embodiments relating to remodeling, an amount and/or rate of remodeling is determined by measuring collagen content in the tissue (which increases upon remodeling), e.g., as exemplified herein.

Examples of respiratory tract remodeling include, without limitation, loss of epithelial integrity, thickening of basement membrane (e.g., lamina reticularis), fibrosis (e.g., subepithelial fibrosis), increased smooth muscle mass, decreased cartilage integrity, and increased airway vascularity (which may potentially contribute to airway obstruction).

Examples of diseases and disorders of the respiratory tract which are associated with respiratory tract remodeling include, without limitation, idiopathic interstitial pneumonia, pulmonary fibrosis (including, for example, idiopathic pulmonary fibrosis and/or autoimmune-related pulmonary fibrosis), drug-induced interstitial lung disease, tuberculosis, chronic obstructive pulmonary disease (COPD), chronic asthma, emphysema, acute lung injury, acute respiratory distress syndrome, and Birt-Hogg-Dube syndrome.

As exemplified in the Examples section herein, cyclic nitroxides are capable of effectively reversing remodeling (e.g., as manifested by increased collagen levels) in different disease models.

Without being bound by any particular theory, it is believed that the anti-remodeling effect of cyclic nitroxides is not exhibited by other compounds reported to have beneficial antioxidant effects.

According to an aspect of some embodiments of the invention, there is provided a cyclic nitroxide compound (according to any of the respective embodiments described herein) for use in treating remodeling of respiratory tract tissue (according to any of the respective embodiments described herein).

According to an aspect of some embodiments of the invention, there is provided a method of treating remodeling of a respiratory tract tissue (according to any of the respective embodiments described herein), the method comprising administering to a subject in need thereof a cyclic nitroxide compound (according to any of the respective embodiments described herein).

In some embodiments of any of the embodiments described herein, the disease or disorder of the respiratory tract is a cancer, and in some embodiments it is a lung cancer.

Examples of respiratory tract cancers treatable according to the present embodiments include, without limitation, small-cell lung carcinoma, non-small-cell lung carcinoma (including adenocarcinoma, squamous cell carcinoma and large-cell carcinoma), laryngeal cancer (e.g., laryngeal squamous cell carcinoma), head and neck cancer (e.g., head and neck squamous cell carcinoma and adenocarcinoma), oropharyngeal cancer and nasopharyngeal carcinoma.

Herein, treatment of a cancer does not include treatment of effects of ionic radiation used to treat the cancer.

In some embodiments of any of the embodiments described herein relating to cancer, the compound described herein is not for use in combination with ionic radiation, e.g., the treatment is devoid of application of ionic radiation.

In some embodiments of any of the embodiments described herein relating to cancer, the cancer is a cancer which is not treated with ionic radiation (e.g., according to accepted practice in the art).

In some embodiments of any of the embodiments described herein relating to cancer, a subject afflicted with cancer is a subject who is not treated with ionic radiation.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In some embodiments of any of the embodiments described herein, treating comprises treating a subject diagnosed with any one or more of the conditions described herein.

In some embodiments of any of the embodiments described herein, treating comprises prophylactic treatment, namely, preventing the appearance of a condition (e.g., fibrosis and/or remodeling according to any of the respective embodiments described herein) in a subject identified as being at risk for the condition, for example, a subject exposed to a substance (e.g., drug, inhaled pollutant, infectious agent) which can lead to the condition, and/or a subject diagnosed with a primary condition that can lead to a secondary condition which the treatment is intended to prevent.

Administration:

The cyclic nitroxide may optionally be administered by local administration to the respiratory tract (e.g., via inhalation) and/or systemic administration (e.g., by oral, intranasal or parenteral administration) wherein a portion of the systemically administered compound reaches the desired respiratory tract area. In some embodiments of any of the embodiments described herein, administration is performed orally, intranasally, by inhalation, or parenterally, for example by intravenous drip or intraperitoneal, subcutaneous, intramuscular or intravenous injection, or topically (including ophthalmically, vaginally, rectally, intranasally). Oral and intranasal administration are exemplary routes of administration which are also particularly convenient for use.

In some embodiments, administration is by oral administration. In some such embodiments, oral administration provides longer lasting therapeutically effective levels of the nitroxide (e.g., in the blood).

Without being bound by any particular theory, it is believed that reduction of nitroxides (e.g., to hydroxylamines) in the gastrointestinal tract is slower than in other parts of the body, such that gradual absorption of the nitroxide in the gastrointestinal tract allows for gradual transfer of the active (non-reduced) nitroxide to the respiratory tract.

In some embodiments of any of the embodiments described herein relating to a treatment, the treatment does not comprise (e.g., is devoid of) administration of a selenium-containing compound, that is, the subject to be treated is a subject who has not received and is not intended to receive a selenium-containing compound (e.g., during the treatment period).

Administration may optionally be effected from 1 to 4 times per day, and/or as needed (e.g., in response to an asthma attack). In some embodiment, administration is effected once or twice per day. In some embodiment, administration is effected twice per day.

Frequency of administration may be determined by the skilled person based on the route of administration (e.g., wherein oral administration provides a longer lasting effect than other routes of administration), formulation (e.g., wherein a sustained release formulation may be administered less frequently) and/or severity of a condition, particularly in view of the guidance provided herein.

In any of the methods and uses described herein, the cyclic nitroxide compounds of the present embodiments can be utilized either per se or as a part of a pharmaceutical composition that further comprises a pharmaceutically acceptable carrier.

Thus, according to additional aspects of the present invention, there is provided pharmaceutical composition, which comprises one or more cyclic nitroxide compounds (according to any of the respective embodiments described herein) and a pharmaceutically acceptable carrier.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration of the composition may be according to any route described herein.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of a disease or disorder of the respiratory tract (according to any of the respective embodiments described herein).

Thus, according to an embodiment of the present invention, the pharmaceutical composition of the present invention is packaged in a packaging material and identified in print, in or on the packaging material, for use in the treatment of a disease or disorder of the respiratory tract (according to any of the respective embodiments described herein).

According to further embodiments of the any of the methods, uses and compositions presented herein, the compounds of the present invention can be combined with other active ingredients which are commonly used to treat a disease or disorder of the respiratory tract (according to any of the respective embodiments described herein).

The terms "comprises", "comprising", "includes", "including", "having" and their conjugates mean "including but not limited to".

The term "consisting of" means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

3-Carbamoyl proxyl (3-CP) was obtained from Sigma-Aldrich.

3-Carbamoyl-2,2,5,5-tetramethyl-3-pyrrolin-1-oxyl (3-CPT) was obtained from Sigma-Aldrich.

Dexamethasone was obtained from Sigma-Aldrich.

Methacholine was obtained from Spectrum Chemicals (New Brunswick, N.J.).

Ovalbumin (Grade V chicken ovalbumin) was obtained from Sigma-Aldrich.

Tempol (TPL) was obtained from Sigma-Aldrich.

Animal Asthma Model:

All experimental procedures were carried out in accordance with the NIH Guidelines for the Care and Use of Laboratory Animals. Specific pathogen-free (SPF) male BALB/c mice (6-7 weeks of age, 18-22 grams), routinely screened serologically for relevant respiratory pathogens, were maintained in an animal housing facility for 1 week before use and given access to food and water ad libitum. Animals were randomly assigned to the indicated experimental groups, and sensitized with two intraperitoneal (IP) injections (20 µg ovalbumin (OVA) emulsified in 2 mg aluminum hydroxide (an adjuvant) in 200 µl phosphate buffer saline (PBS), pH 7.4), on days 1 and 10.

After another week, the animals were challenged by exposure to ovalbumin (OVA) aerosol (1%, w/v, in PBS) for 30 minutes each day on days 17, 18 and 19, in order to elicit an inflammatory reaction in the lungs characterized by airway hyper-responsiveness (AHR), an influx of inflammatory cells (particularly eosinophils), and increased pulmonary levels of various cytokines and transforming growth factors, protein nitration and lipid peroxidation.

In a longer (chronic) murine model, mice were challenged 3 times a week for 4-5 weeks.

The features of allergic inflammation typically reached their peak a day or two after the final exposure. Mice were then subjected to one of the following treatments: (i) sham-sensitization plus challenge with PBS; (ii) positive control-sensitization plus challenge with OVA; (iii) sensitization plus challenge with OVA and various indicated treatments (e.g., with nitroxide or dexamethasone), including different modes (oral, IP, intranasal, inhalation), time windows (sensitization stage, challenge stage, both stages and after the last challenge), and doses of nitroxide administration.

Evaluation of Respiratory Activity and Airway Hyper-responsiveness (AHR):

One day after the final challenge, respiratory activity and airway hyper-responsiveness (AHR) of experimental animals were evaluated. Whole body plethysmographs for enhanced pause (Penh) measurements are often used for assessment of AHR. However, critics have questioned the validity of Penh measurements, which supposedly measure airway obstruction of live non-sedated mice, stating that it is likely to measure the distress of the animal rather than actual obstruction. Instead, it is suggested to measure the lung mechanics using the forced oscillation technique in anesthetized, tracheostomized, paralyzed animals. In brief, mice were sedated with an intraperitoneal (IP) injection of xylazine hydrochloride and anaesthetized with IP injection of pentobarbital. Subsequently, the animals were tracheostomized using an 18 gauge cannula, ventilated with a FlexiVent™ apparatus (SCIREQ), and muscle paralysis was induced with pancuronium bromide. The mice were ventilated in a quasi-sinusoidal fashion with the following settings: a tidal volume of 10 ml/kg, maximum inflation pressure of 3 millibar (30 cm $H_2O$), a positive end expiratory pressure (PEEP) of 3 millibar and a frequency of 150 per minute. Following an equilibration period of 3 minutes of tidal ventilation, two lung inflations to a transrespiratory pressure of 2.5 millibar were performed and baseline measurements were taken. Airway hyper-responsiveness (AHR) was determined by aerosolizing increasing concentrations of methacholine. After baseline determination of airway resistance, mice were challenged with 0 to 64 mg/mL methacholine nebulized directly into the ventilatory circuit using an AeroNeb™ Lab nebulizer system (SCIREQ). Two models of respiratory mechanics were used to assess lung resistance: a linear 1st-order single compartment model and a constant-phase model. All data points were collected with FlexiVent™ software (SCIREQ).

Bronchoalveolar Lavage (BAL) Fluid Assays:

Bronchoalveolar lavage (BAL) fluid (also referred to herein as "BALf") and bronchial submucosal inflammation are characteristic features of asthma. Mice were euthanized with an overdose of 50 mg/kg pentobarbital and ice-cold phosphate buffer saline (PBS) (0.6 ml) was instilled into the lungs. BAL fluid was obtained by three aspirations via tracheal cannulation, centrifuged, and the supernatant collected and stored at −70° C. Cell pellets were re-suspended in PBS and 100 µl aliquots placed onto slides and centrifuged (200 g, 4° C., 10 minutes) in a cytospin machine. Induction of oxidative stress was evaluated using a 2',7'-dichlorofluorescein fluorescence assay, and total IgE, IgG2a, panel of cytokines, transforming growth factors, collagen, protein nitration and lipid peroxidation were measured using commercial kits according to the manufacturer's recommendations. A Sircol™ collagen assay kit was obtained from Biocolor Life Sciences Assays, a protein nitration assay kit was obtained from Abcam, and other assay kits were obtained from PeproTech Asia.

Lung Tissue Histopathology:

Following aspiration of BAL as described hereinabove, a thoracotomy was performed, and the right main bronchus was tied. The left lung was fixed by means of intrabronchial infusion with 1 ml of 4% formaldehyde, and then immersed in fixative (10% (v/v) neutral buffered formalin) for 24 hours at 4° C. Transverse sections of the left lung were embedded in paraffin, and 4-6 mm sections were stained with hematoxylin and eosin (H&E) by Hadassah Hospital Pathology Service (Jerusalem, Israel). In addition, periodic acid-Schiff (PAS) staining was performed on lung tissue, and the degree of mucin production was measured from PAS staining.

Nitroxide Concentration Measurement:

Electron paramagnetic resonance (EPR) spectroscopy was used to determine residual levels of nitroxide in mouse tissue. Blood samples or tissue samples were diluted with 0.5 ml phosphate buffer (40 mM, pH 7.4) or water, inserted into a flexible capillary placed in a quartz tube installed within the EPR spectrometer cavity and assayed for residual nitroxide. A similar procedure was used to determine the residual nitroxide in tissue homogenates of various organs, which were corrected for blood contamination spectrophotometrically by following the absorption of oxyhemoglobin at 400-600 nm. Measured EPR signals were compared to those of a nitroxide standard solution.

In order to determine total hydroxylamine and nitroxide concentrations, 2 mM $K_3Fe(CN)_6$ was added to samples in order to oxidize hydroxylamines to the respective nitroxide, and the nitroxide level was determined by EPR spectroscopy as described hereinabove.

Example 1

Effects of Tempol (TPL) and 3-carbamoyl proxyl (3-CP) on Pulmonary Inflammation in Murine Asthma Model The effects of the nitroxides Tempol (TPL) and 3-carbamoyl proxyl (3-CP) were studied using an ovalbumin-induced murine model of asthma as described hereinabove in the Materials and Methods section.

Control and experimental groups contained 10 mice each. The effects of the nitroxides were investigated by feeding the mice ad libitum a diet of nitroxide-containing chow (1 weight percent) during both ovalbumin (OVA)-induced sensitization and challenging periods (days −2-19), during the sensitization period (days −2-11) or challenge period (days 13-19). Nitroxide-containing chow were prepared by dissolving 500 grams chow in a minimum volume of water containing 5 grams nitroxide and 5 grams commercial chicken soup powder, preparing the chow and drying it at 37° C. (animals were reluctant to eat nitroxide-containing chow until chicken soup powder was added).

3-CP was also administered using 3 daily intraperitoneal (IP) injections (200 μl, 0.15 M, ~300 mg/kg) 0.5 hour prior to the challenge with OVA aerosol, or by nasal instillation (50 μl, 0.3 M, ~150 mg/kg) twice a day 0.5 hour prior to the challenge with OVA aerosol and 6 hours later without exceeding its maximally tolerated dose, which has been previously established to be 300-500 mg/kg. Both 3-CP and TPL were non-toxic when administered orally or via IP injection to untreated OVA-challenged mice for 22 days.

As shown in FIG. 1, detectable levels of the nitroxides 3-CP and TPL were observed in the blood of mice following oral administration of nitroxides, with 3-CP blood concentrations being higher than TPL blood concentrations.

The residual concentration of 3-CP in the lungs was about 65% of that in the blood, and significantly higher than in the heart, spleen, liver, kidney and brain (in that order). The residual concentrations of the respective hydroxylamines of 3-CP and TPL were higher than those of the therapeutically active nitroxide free radical (data not shown), indicating that most of the nitroxides had been reduced to a hydroxylamine.

As shown in FIG. 2, the residual concentration of 3-CP in the blood and lung tissue upon nasal instillation (50 μL, 0.3 M) decreased exponentially with time. As further shown therein, the rate of the reduction/clearance of 3-CP from the blood was similar to the rate of the reduction/clearance from lung tissue, being characterized by a half-life of about 80 minutes, with the absolute concentration of the nitroxide in lung tissue consistently being about twice the concentration in the blood.

In view of the abovementioned 80 minute half-life, treatment of the OVA-challenged mice included nasal instillation of 3-CP (50 μL, 0.3 M) twice a day 0.5 hour before and 6 hours after the OVA challenge.

The effects of 3-CP and TPL were further evaluated by measuring lung resistance in methacholine-challenged mice according and total inflammatory cell counts and eosinophil counts in bronchoalveolar lavage (BAL) fluid following oral administration of each nitroxide, according to procedures described hereinabove. OVA inhalation markedly increased total inflammatory cell counts and particularly eosinophil counts, as compared to mice treated by saline aerosol control.

As shown in FIG. 3, both 3-CP and TPL suppressed methacholine-induced increase in lung resistance in mice with OVA-induced asthma, with 3-CP being considerably more effective than TPL.

Similarly, as shown in FIG. 4, both 3-CP and TPL suppressed attenuated the increase in total inflammatory cell counts and eosinophil counts induced by OVA inhalation, with 3-CP being considerably more effective than TPL.

These results indicate that 3-CP is more effective than TPL in reversing asthma symptoms.

The efficacy of oral administration of 3-CP (1 weight percent in chow) during the sensitization period and/or challenge period was then compared to IP injection (~300 mg/kg, 0.5 hour before the OVA challenge) or intranasal instillation (~150 mg/kg, 0.5 hour before the OVA and 6 hours later) of 3-CP, as well as to dexamethasone treatment (1 mg/kg, 3 daily IP injections, 0.5 hour prior to the challenge with OVA aerosol).

As shown in FIGS. 5 and 6, oral administration of 3-CP during both the sensitization period and challenge period was more effective than IP injection or intranasal instillation of 3-CP, oral administration of 3-CP during the sensitization period or challenge period alone, or treatment with dexamethasone, as determined by measuring levels of inflammatory cells (FIG. 5) and lung resistance (FIG. 6). As further shown therein, intranasal instillation of 3-CP and dexamethasone treatment had similar anti-inflammatory effects.

As further shown in FIG. 5, oral administration of 3-CP during both the sensitization period and challenge period was more effective than treatment with dexamethasone at reducing inflammatory response.

These results indicate that 5-membered cyclic nitroxides such as 3-CP are particularly effective at reducing respiratory inflammatory responses.

Example 2

Effect of 3-CP on Pulmonary Levels of Inflammation-associated cytokines in Asthma Model In order to assess the effect of 3-CP on inflammatory signaling pathways, levels of the cytokines TGF-β1, IL-4, IL-5, IL-13 and IFN-γ in BAL fluid were determined according to procedures described hereinabove, upon oral, intranasal or IP administration of 3-CP.

TGF-β1 is a multifunctional cytokine that plays key roles in diverse biological processes, including tissue remodeling and repair [Homer & Elias, *Physiology* (*Bethesda*) 2005, 20:28-35; Lee et al., *Proc Am Thorac Soc* 2006, 3:418-423]. In human chronic lung diseases such as asthma, TGF-β1 expression increases and correlates with disease severity and the degree of peribronchial fibrosis [Minshall et al., *Am J Respir Cell Mol Biol* 1997, 17:326-333].

The effects of 3-CP on cytokine levels are summarized in Table 1 below.

TABLE 1

Effect of oral, intraperitoneal (IP) and intranasal (IN) administration of 3-CP during sensitization (S) and/or challenge (C) with ovalbumin (OVA) on IL-4, IL-5, IL-13, TGF-β1 and IFN-γ levels (ng/mg) in lung tissue

|  | IL-13 | IL-4 | IL-5 | IFN-γ | TGF-β1 |
|---|---|---|---|---|---|
| Saline (control) | 1.39 ± 0.07* | 1.09 ± 0.13* | 1.60 ± 0.09* | 6.42 ± 0.28* | 0.58 ± 0.07* |
| OVA | 2.50 ± 0.1 | 2.87 ± 0.19 | 3.51 ± 1.5 | 4.43 ± 0.31 | 1.28 ± 0.16 |
| OVA oral-S&C | 1.67 ± 0.08* | 1.65 ± 0.12* | 1.96 ± 0.17* | 5.60 ± 0.22* | 0.73 ± 0.07* |
| OVA oral-S | 2.20 ± 0.07* | 2.44 ± 0.09 | 3.16 ± 0.07 | 3.78 ± 0.27 | 0.76 ± 0.02* |
| OVA oral-C | 2.01 ± 0.26* | 2.03 ± 0.28 | 2.40 ± 0.06* | 5.32 ± 0.38* | 0.72 ± 0.08* |
| OVA IP-C | 1.38 ± 0.10* | 1.70 ± 0.15* | 2.08 ± 0.27* | 5.17 ± 0.19* | 0.88 ± 0.05* |
| OVA IN-C | 1.99 ± 0.07* |  |  |  |  |
| OVA IP-Dex | 1.80 ± 0.06* |  |  |  |  |

*p < 0.05 compared to untreated OVA-challenged mice
Dex = dexamethasone

As shown in FIGS. 7A-7E and in Table 1, 3-CP inhibited OVA-induced increases in the levels of IL-4 (FIG. 7A), IL-5 (FIG. 7B), IL-13 (FIG. 7D) and TGF-β1 (FIG. 7E) in lung tissue, as well as the OVA-induced decrease in the level of INF-y (FIG. 7C) in lung tissue.

As further shown therein, oral administration of 3-CP was consistently more effective than IP injection of 3-CP at modulating levels of each of the examined cytokines.

Figure 7A:
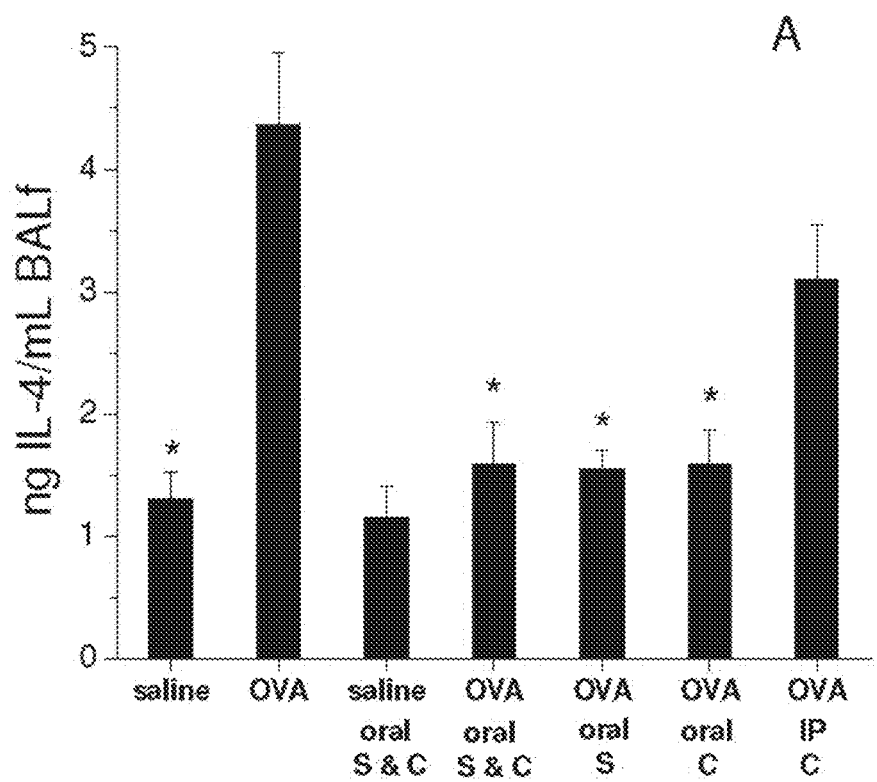
Figure 7B:
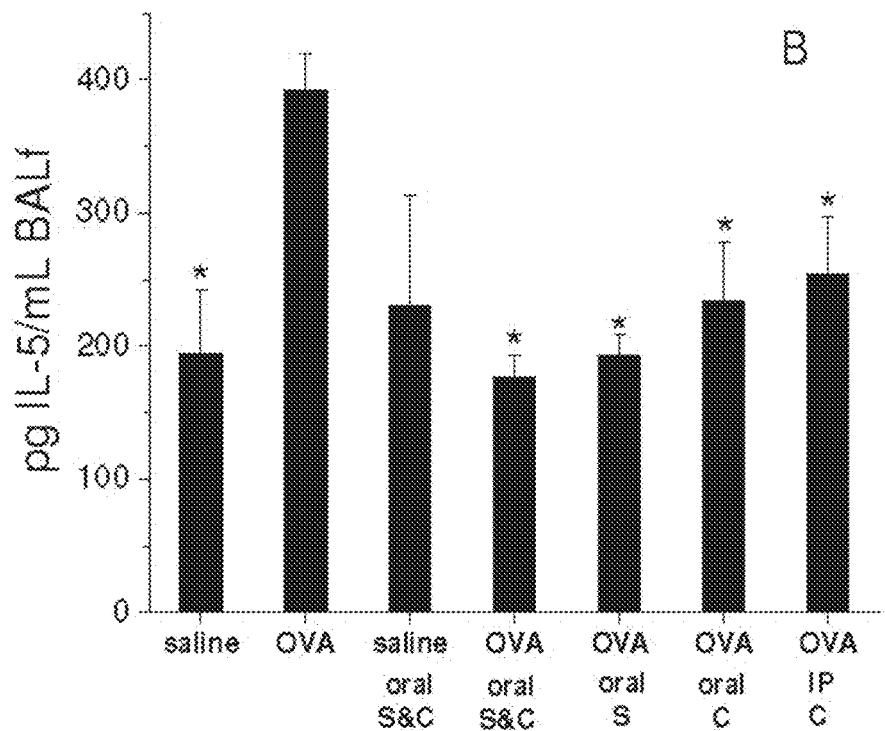
Figure 7C:
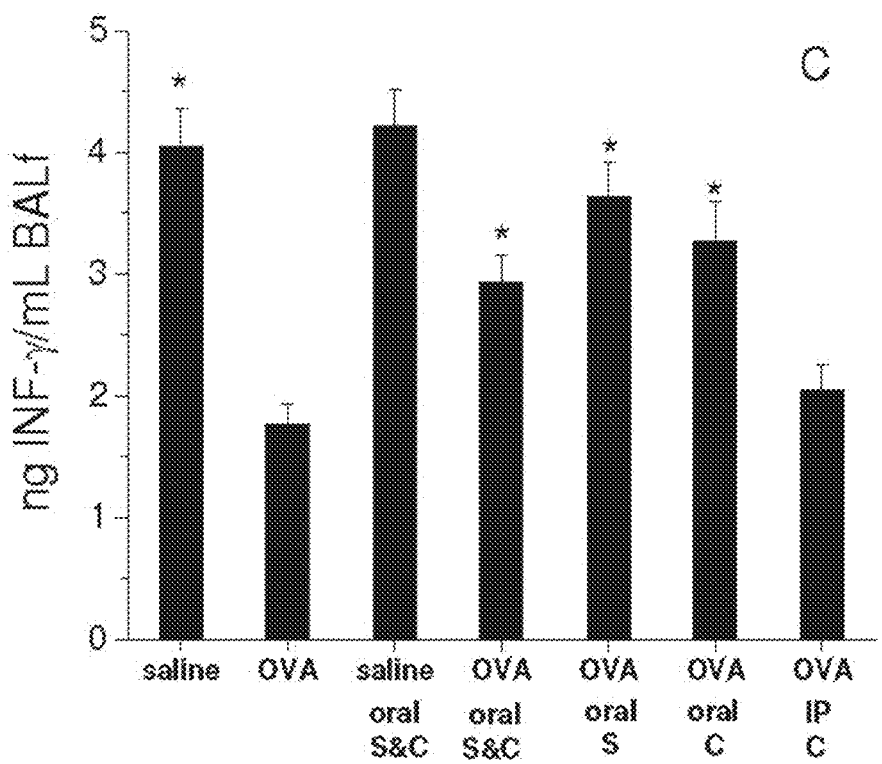
Figure 7D:
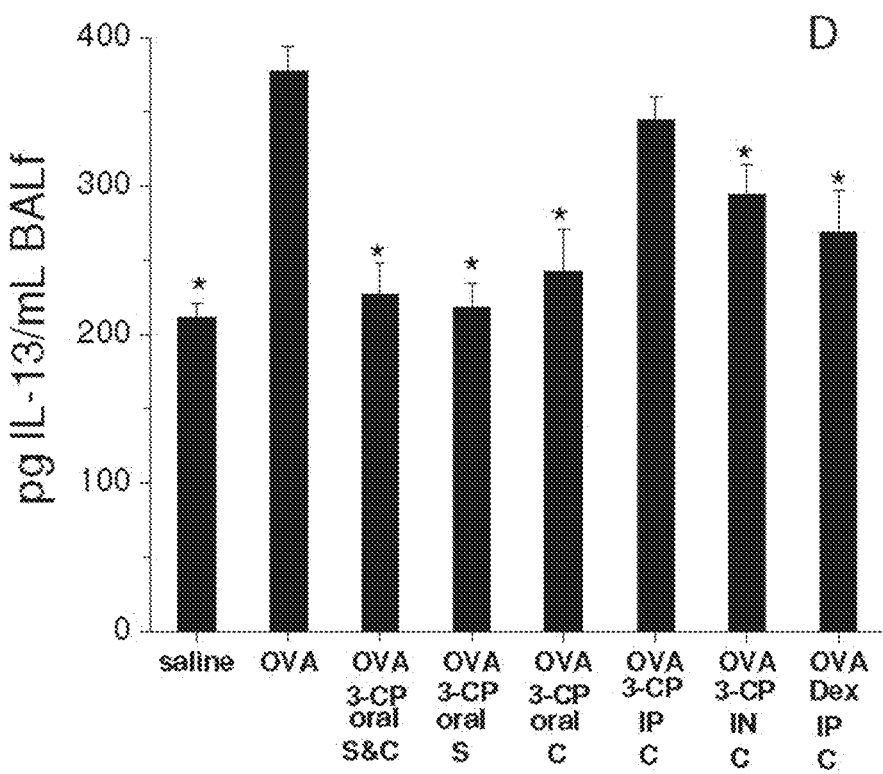
Figure 7E:
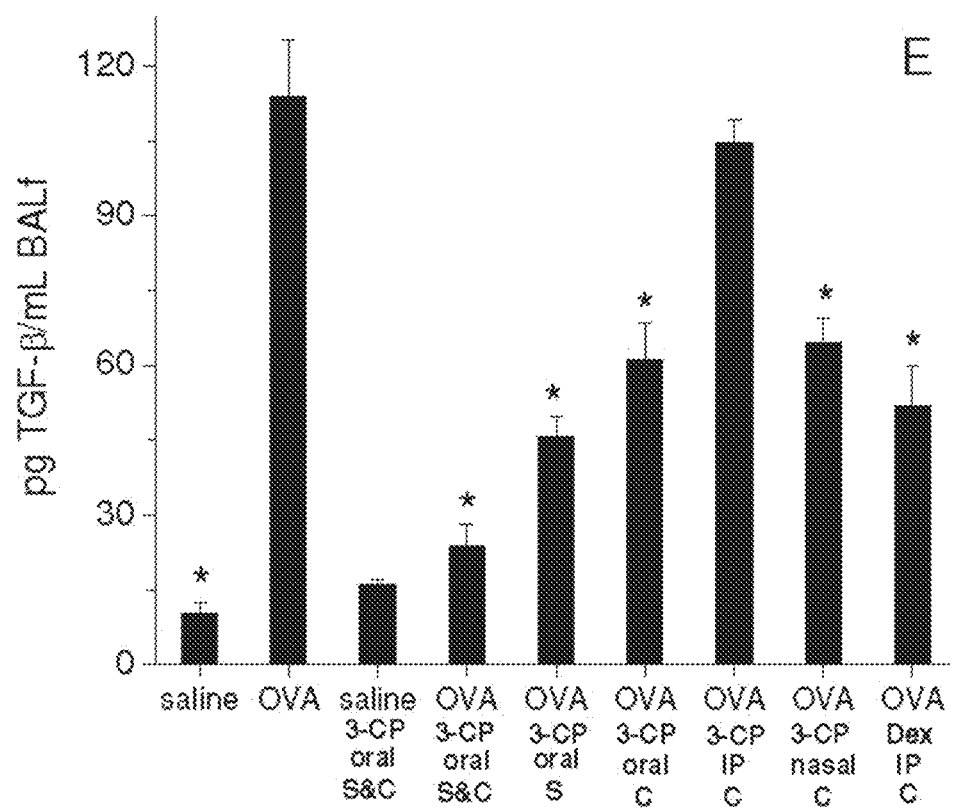

As further shown in FIGS. 7D and 7E and in Table 1, oral administration of 3-CP was also more effective than intranasal instillation of 3-CP and IP injection of dexamethasone at reducing levels of IL-13 (FIG. 7D) and TGF-β1 (FIG. 7E).

These results indicate that 5-membered cyclic nitroxides such as 3-CP are effective at cytokine-mediated pro-inflammatory pathways in the lung.

Example 3

Effect of 3-CP on Protein Nitration in Lung in Asthma Model

In order to determine whether 3-CP reduces protein nitration, a form of cell damage induced by peroxynitrite (an anion generally believed to be formed in vivo by a reaction of superoxide radical and nitric oxide), lung homogenates were assayed for 3-nitrotyrosine (3-NT) levels.

As shown in FIG. 8, challenge with OVA significantly increased pulmonary levels of 3-NT in mice, as compared to control mice treated with saline aerosol control (with or without 3-CP).

As further shown therein, 3-CP administered via all tested modes of delivery markedly suppressed 3-NT levels as compared to the vehicle control as well as treatment with dexamethasone.

These results indicate that 3-CP reduces oxidative stress in the lung associated with protein nitration and peroxynitrite.

Example 4

Effect of 3-CP on Lung Pathology in Asthma Model

In order to evaluate the effect of 3-CP on lung pathology, animals in an ovalbumin-induced asthma model were treated with 3-CP, and killed by abdominal aortic transaction and exsanguination, according to procedures described hereinabove. Lung tissue was examined by hematoxylin and eosin (H&E) staining, the degree of mucin production was determined from periodic-acid-Schiff (PAS) staining.

As shown in FIG. 9, 3-CP administered via all tested modes of delivery reduced the degree of lung pathology in asthmatic mice, as determined by H & E pathology scoring, and 3-CP was more effective in this respect than treatment with dexamethasone.

Similarly, as shown in FIGS. 10 and 11, 3-CP administered via all tested modes of delivery reduced the mucin levels in asthmatic mice, as determined by PAS scoring. As further shown in FIG. 10, 3-CP was at least as effective as dexamethasone in reducing mucin levels.

These results further indicate that 3-CP protects lungs against inflammation-associated damage.

Example 5

Effects of 3-carbamoyl-2,2,5,5-tetramethyl-3-pyrrolin-1-oxyl (3-CPT) on Lungs

Another 5-membered nitroxide derivative, 3-carbamoyl-2,2,5,5-tetramethyl-3-pyrrolin-1-oxyl (3-CPT), was tested in accordance with procedures described hereinabove. Oral administration of 3-CPT was effected by feeding mice chow with 0.7 weight percent 3-CPT.

The in vivo half-life of 3-CPT was similar to that of 3-CP (as described in Example 1), but 3-CPT exhibited lower water-solubility than 3-CP (data not shown).

As shown in FIG. 12, the concentration of 3-CPT in the blood of mice fed chow with 0.7 weight percent 3-CPT) was similar to that of the concentration of 3-CP in mice fed chow with 1 weight percent 3-CP (as shown in FIG. 1).

As further shown in FIG. 12, most of the 3-CPT in the blood was reduced to the respective hydroxylamine (similarly to 3-CP, as described in Example 1).

These results indicate that 3-CP and 3-CPT behave similarly in vivo.

As shown in FIG. 13, oral administration of 3-CPT was effective in reversing OVA-induced increase of total cell counts in BAL fluid.

As shown in FIG. 14, oral administration of 3-CPT reduced methacholine-induced lung resistance, albeit to a considerably lesser degree than 3-CP.

Example 6

Effects of 3-CP in In Vivo Model of Severe (Chronic) Asthma

In order to evaluate the effects of 3-CP in severe (chronic) asthma, an in vivo model was used in which mice were administered two IP injections of 10 μg OVA and 1 mg Al(OH)$_3$ in 0.5 ml saline at days 1 and 10. After the sensitization, the mice were challenged with OVA aerosols (2% in saline, 4 ml) 3 times per week for an additional 4 weeks.

3-CP was administered orally (1 weight percent in chow) during the entire experiment, and dexamethasone (Dex) was administered via IP injection (1 mg/kg) one hour before each challenge. Inflammatory cell counts and pulmonary collagen content were then evaluated according to procedures described hereinabove, in order to assess effects on inflammation and remodeling, respectively.

As shown in FIGS. 15A and 15B, 3-CP reduced inflammatory cell counts, and especially eosinophil counts (FIG. 15B), in the BAL fluid of mice with OVA-induced chronic asthma, and was at least as effective as dexamethasone in this respect.

As shown in FIG. 16, 3-CP completely reversed the increase in collagen content of the lung in mice with OVA-induced chronic asthma, and was more effective than dexamethasone treatment at reducing collagen content.

These results indicate that nitroxides such as 3-CP are effective at treating severe and/or chronic respiratory diseases and disorders, and are capable of reversing remodeling processes in the respiratory tract.

Example 7

Effects of 3-CP in In Vivo Model of Pulmonary Fibrosis

In order to evaluate the effects of 3-CP in interstitial lung disease, an in vivo pulmonary fibrosis model was used in which mice (initial weight 25-28 grams) were administered intra-tracheally (under light sedation) a dose of 3 mg/kg bleomycin in 50 μl of sterile saline. The experiment duration was 14 days. 3-CP (150 mg/kg) was administered daily via intranasal instillation. Each experimental group included 15-20 mice.

The effect of 3-CP on bleomycin-induced inflammation was evaluated by determining lung resistance, total inflammatory cell count, and TGF-β1 levels, according to procedures described hereinabove.

As shown in FIG. 17, 3-CP administration completely reversed the bleomycin-induced increase in lung resistance.

As shown in FIG. 18, 3-CP significantly reduced the bleomycin-induced increase in inflammatory cell counts in BAL fluid.

As shown in FIG. 19, 3-CP significantly reduced the bleomycin-induced increase in TGF-β1 expression in lungs.

The degree of fibrosis was evaluated by measuring collagen content in lung tissue.

As shown in FIG. 20, 3-CP significantly inhibited bleomycin-induced pulmonary fibrosis, as determined by pulmonary collagen content.

These results indicate that nitroxides such as 3-CP are effective at treating interstitial lung diseases and disorders such as pulmonary fibrosis, and at inhibiting associated pulmonary remodeling processes.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a disease or disorder of the respiratory tract, said disease or disorder being an obstructive lung disease or disorder, the method comprising administering to a subject in need thereof a compound having the general formula I:

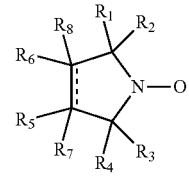

Formula I wherein:
the dashed line denotes a saturated bond or an unsaturated bond, wherein when the dashed line denotes an unsaturated bond, $R_7$ and $R_8$ are absent;

$R_1$-$R_4$ are each independently a $C_{1-4}$-alkyl, or alternatively, $R_1$ and $R_2$, and/or $R_3$ and $R_4$, together form a 3-7-membered alicyclic ring; and $R_5$-$R_8$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, —S(=O)—R', —S(=O)$_2$—R', —S(=O)$_2$—O—R', —O—S(=O)$_2$—O—R', cyano, nitro, azide, —P(=O)(OR')(OR''), —C(=O)—R', —C(=S)—R', —N(R')—C(=O)—NR''R''', —N(R')—C(=S)—NR''R''', —OC(=O)—NR'R'', —N(R'')—C(=O)OR', —OC(=S)—NR'R'', —N(R'')—C(=S)OR', —C(=O)—NR'R'', —NR''—C(=O)R', —C(=O)—OR', —O—C(=O)R', —S(=O)$_2$—NR'R'', —NR''—S(=O)$_2$R', —N(R')—N (R''')R''', —N⁺R'R''R''' and —NR'R'', wherein at least one of $R_5$-$R_8$ is —C(=O)—NR'R'', wherein R', R'' and R''' are each independently hydrogen, alkyl, alkenyl, alkynyl, cycloalkyl, heteroalicyclic, aryl and/or heteroaryl, each of said alkyl, said alkenyl, said alkynyl, said cycloalkyl, said heteroalicyclic, said aryl, said heteroaryl, said alkoxy, said aryloxy, said thiohydroxy and said thioaryloxy being unsubstituted, thereby treating the disease or disorder.

2. The method of claim 1, wherein said dashed line denotes a saturated bond.

3. The method of claim 1, wherein said —C(=O)—NR'R'' is —C(=O)NH₂.

4. The method of claim 1, wherein $R_1$-$R_4$ are each methyl.

5. The method of claim 1, wherein $R_6$ is hydrogen, and each of $R_7$ and $R_8$ is either hydrogen or absent.

6. The method of claim 1, wherein the compound is 3-carbamoyl-2,2,5,5-tetramethyl-pyrrolidin-1-oxyl.

7. The method of claim 1, wherein said disease or disorder of the respiratory tract is an inflammatory disease or disorder of the respiratory tract.

8. The method of claim 1, wherein said disease or disorder of the respiratory tract is associated with respiratory tract remodeling.

9. The method of claim 8, wherein said disease or disorder of the respiratory tract is selected from the group consisting of chronic obstructive pulmonary disease (COPD) and chronic asthma.

10. The method of claim 1, wherein said obstructive lung disease or disorder is selected from the group consisting of asthma, bronchitis, bronchiectasis, and chronic obstructive pulmonary disease (COPD).

11. The method of claim 1, wherein said disease or disorder of the respiratory tract is associated with a hypersensitivity reaction.

12. The method of claim 1, wherein said administering comprises oral and/or intranasal administration of the compound.

13. The method of claim 1, wherein said treating does not comprise administration of a selenium-containing compound.

14. A method of treating a disease or disorder associated with respiratory tract remodeling, the method comprising administering by oral and/or intranasal administration to a subject in need thereof a cyclic nitroxide compound having the general formula I:

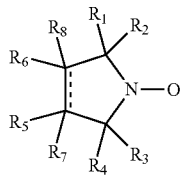

Formula I wherein:
the dashed line denotes a saturated bond or an unsaturated bond, wherein when the dashed line denotes an unsaturated bond, $R_7$ and $R_8$ are absent;
$R_1$-$R_4$ are each independently a $C_{1-4}$-alkyl, or alternatively, $R_1$ and $R_2$, and/or $R_3$ and $R_4$, together form a 3-7-membered alicyclic ring; and
$R_5$-$R_8$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, —S(=O)—R', —S(=O)₂—R', —S(=O)₂—O—R', —O—S(=O)₂—O—R', cyano, nitro, azide, —P(=O)(OR')(OR''), —C(=O)—R', —C(=S)—R', —N(R')—C(=O)—NR''R''', —N(R')—C(=S)—NR''R''', —OC(=O)—NR'R'', —N(R'')—C(=O)OR', —OC(=S)—NR'R'', —N(R'')—C(=S)OR', —C(=O)—NR'R'', —NR''—C(=O)R', —C(=O)—OR', —O—C(=O)R', —S(=O)₂—NR'R'', —NR''—S(=O)₂R', —N(R')—N(R'')R''', —N⁺R'R''R''' and —NR'R'', wherein R', R'' and R''' are each independently hydrogen, alkyl, alkenyl, alkynyl, cycloalkyl, heteroalicyclic, aryl and/or heteroaryl, each of said alkyl, said alkenyl, said alkynyl, said cycloalkyl, said heteroalicyclic, said aryl, said heteroaryl, said alkoxy, said aryloxy, said thiohydroxy and said thioaryloxy being unsubstituted, wherein said disease or disorder is selected from the group consisting of idiopathic interstitial pneumonia, autoimmune-related pulmonary fibrosis, drug-induced interstitial lung disease, chronic obstructive pulmonary disease (COPD), chronic asthma, emphysema, acute lung injury, acute respiratory distress syndrome, and Birt-Hogg-Dube syndrome, thereby treating the disease or disorder.

15. The method of claim 14, wherein at least one of $R_5$-$R_8$ is —C(=O)—NR'R''.

16. The method of claim 15, wherein said —C(=O)—NR'R'' is —C(=O)NH₂.

17. The method of claim 14, wherein $R_1$-$R_4$ are each methyl.

18. The method of claim 14, wherein $R_6$ is hydrogen, and each of $R_7$ and $R_8$ is either hydrogen or absent.

19. The method of claim 14, wherein the compound is selected from the group consisting of 3-carbamoyl-2,2,5,5-tetramethyl-pyrrolidin-1-oxyl and 3-carbamoyl-2,2,5,5-tetramethyl-3-pyrrolin-1-oxyl.

20. The method of claim 14, wherein said treating does not comprise administration of a selenium-containing compound.

21. A method of treating asthma, chronic obstructive pulmonary disease (COPD), and/or lung cancer, the method comprising administering to a subject in need thereof a cyclic nitroxide compound having the general formula I:

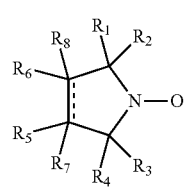

Formula I wherein:
the dashed line denotes a saturated bond or an unsaturated bond, wherein when the dashed line denotes an unsaturated bond, $R_7$ and $R_8$ are absent;
$R_1$-$R_4$ are each independently a $C_{1-4}$-alkyl, or alternatively, $R_1$ and $R_2$, and/or $R_3$ and $R_4$, together form a 3-7-membered alicyclic ring; and
$R_5$-$R_8$ are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, —S(=O)—R', —S(=O)$_2$—R', —S(=O)$_2$—O—R', —O—S(=O)$_2$—O—R', cyano, nitro, azide, —P(=O)(OR')(OR"), —C(=O)—R', —C(=S)—R', —N(R')—C(=O)—NR"R'", —N(R')—C(=S)—NR"R'", —OC(=O)—NR'R", —N(R")—C(=O)OR', —OC(=S)—NR'R", —N(R")—C(=S)OR', —C(=O)—NR'R", —NR"—C(=O)R', —C(=O)—OR', —O—C(=O)R', —S(=O)$_2$—NR'R", —NR"—S(=O)$_2$R', —N(R')—N(R")R'", —N$^+$R'R"R'" and —NR'R", wherein R', R" and R'" are each independently hydrogen, alkyl, alkenyl, alkynyl, cycloalkyl, heteroalicyclic, aryl and/or heteroaryl, each of said alkyl, said alkenyl, said alkynyl, said cycloalkyl, said heteroalicyclic, said aryl, said heteroaryl, said alkoxy, said aryloxy, said thiohydroxy and said thioaryloxy being unsubstituted, thereby treating the asthma, chronic obstructive pulmonary disease (COPD), and/or lung cancer.

22. The method of claim 21, wherein at least one of $R_5$-$R_8$ is —C(=O)—NR'R".

23. The method of claim 22, wherein said —C(=O)—NR'R" is —C(=O)NH$_2$.

24. The method of claim 21, wherein $R_1$-$R_4$ are each methyl.

25. The method of claim 21, wherein $R_6$ is hydrogen, and each of $R_7$ and $R_8$ is either hydrogen or absent.

26. The method of claim 21, wherein the compound is selected from the group consisting of 3-carbamoyl-2,2,5,5-tetramethyl-pyrrolidin-1-oxyl and 3-carbamoyl-2,2,5,5-tetramethyl-3-pyrrolin-1-oxyl.

27. The method of claim 21, wherein said administering comprises oral and/or intranasal administration of the compound.

28. The method of claim 21, wherein said treating does not comprise administration of a selenium-containing compound.

* * * * *